US008178516B2

(12) United States Patent
Shapiro

(10) Patent No.: US 8,178,516 B2
(45) Date of Patent: *May 15, 2012

(54) COMPOSITIONS AND METHOD FOR TREATMENT OF CHRONIC INFLAMMATORY DISEASES

(75) Inventor: Howard K. Shapiro, Narberth, PA (US)

(73) Assignee: Sylvan Labs, LLC, Levittown, PA (US)

( * ) Notice: Subject to any disclaimer, the term of this patent is extended or adjusted under 35 U.S.C. 154(b) by 621 days.

This patent is subject to a terminal disclaimer.

(21) Appl. No.: 12/070,518

(22) Filed: Feb. 20, 2008

(65) Prior Publication Data

US 2008/0234380 A1  Sep. 25, 2008

Related U.S. Application Data

(63) Continuation-in-part of application No. 10/924,945, filed on Aug. 24, 2004, now abandoned, which is a continuation-in-part of application No. 09/610,073, filed on Jul. 5, 2000, now abandoned, which is a continuation-in-part of application No. 08/814,291, filed on Mar. 10, 1997, now abandoned, which is a continuation-in-part of application No. 08/241,603, filed on May 11, 1994, now abandoned, which is a continuation-in-part of application No. 07/906,909, filed on Jun. 30, 1992, now abandoned.

(51) Int. Cl.
*A01N 37/44* (2006.01)
*A61K 31/196* (2006.01)
*C07C 229/34* (2006.01)
*C07C 229/38* (2006.01)
*C07C 229/42* (2006.01)
*C07C 229/60* (2006.01)

(52) U.S. Cl. ........ 514/162; 514/166; 514/567; 562/442; 562/458

(58) Field of Classification Search .................. None
See application file for complete search history.

(56) References Cited

U.S. PATENT DOCUMENTS

| | | | | |
|---|---|---|---|---|
| 3,846,541 A | * | 11/1974 | Howard | 514/543 |
| 4,200,647 A | * | 4/1980 | Bollag et al. | 514/549 |
| 4,276,284 A | * | 6/1981 | Brown | 514/8 |
| 4,738,850 A | * | 4/1988 | Thakur et al. | 424/468 |
| 5,053,429 A | * | 10/1991 | Hirsch et al. | 514/562 |
| 5,626,884 A | * | 5/1997 | Lockett | 424/639 |
| 5,668,117 A | * | 9/1997 | Shapiro | 514/55 |
| 6,090,414 A | * | 7/2000 | Passwater et al. | 424/702 |
| 6,444,221 B1 | * | 9/2002 | Shapiro | 424/451 |
| 2006/0034872 A1 | * | 2/2006 | Woolf | 424/400 |

FOREIGN PATENT DOCUMENTS

| | | | |
|---|---|---|---|
| GB | 1033843 | * | 5/1965 |
| GB | 2060635 | * | 5/1981 |
| JP | 05-000954 | * | 5/1993 |

OTHER PUBLICATIONS

Wiesel et al., "The Synergistic Action of Para-aminobenzoic Acid and Cortisone in the treatment of Rheumatoid Arthritis" The American Journal of the Medical Sciences, (1951) vol. 227, No. 1, pp. 243-248.*
Zarafonetis et al., "Clinical Use of Para-aminobenzoic Acid" Texas State Journal of Medicine (1953) vol. 49, pp. 666-672.*
Brahn, "Animal Models of Rheumatoid Arthritis" Clinical Orthopaedics and Related Research (1991) vol. 265, pp. 42-53.*
"Drug details—Cortisone Acetate" Drugs@FDA, posted online at http://www.accessdata.fda.gov/scripts/cder/drugsatfda/index.cfm?fuseaction=Search.DrugDetails.*
Wu et al., "Antioxidative Properties of Acetylsalicylic Acid on Vascular Tissues From Normotensive and Spontaneously Hypertensive Rats" Circulation (2002) vol. 105 pp. 387-392.*
English language abstract of JP05-000954, published 1993, downloaded from CAS.*
Martin et al., "Antibacterial Activity of Substances Related to p-Aminobenzoic Acid" Biochemical Journal (1945) vol. 39 No. 1 pp. 91-95.*
Peppercorn, M., "Advances in Drug Therapy for Inflammatory Bowel Disease" Annals of Internal Medicine (1990) vol. 112 pp. 50-60.*
Mann et al., Molecular Amplifiers: Synthesis and Functionalization of a Poly(aminopropyl)dextran Bearing a Uniquely Reactive Terminus for Univalent Attachment to Biomolecules Bioconjugate Chemistry (1992) vol. 3 pp. 154-159.*
"Drug details—Cortisone Acetate" Drugs@FDA, posted online at http://www.accessdata.fda.gov/scripts/cder/drugsatfda/index.cfm?fuseaction=search.DrugDetails downloaded Nov. 27, 2006.*

* cited by examiner

*Primary Examiner* — Eric S Olson

(57) ABSTRACT

This invention defines novel compositions that can be used for clinical treatment of a class of chronic inflammatory diseases. Increased generation of carbonyl substances, namely aldehydes and ketones, occurs at sites of chronic inflammation and is common to the etiologies of all of the clinical disorders addressed herein. Such carbonyl substances are cytotoxic and additionally serve to perpetuate and disseminate the inflammatory process. This invention defines use of compositions, the orally administered required primary agents of which are primary amine derivatives of benzoic acid capable of covalently reacting with the carbonyl substances. p-Aminobenzoic acid (or PABA) is an example of the required primary agent of the present invention. PABA has a small molecular weight, is water-soluble, has a primary amine group which reacts with carbonyl-containing substances and is tolerated by the body in relatively high dosages for extended periods. The method of the present invention includes administration of a composition comprising: (1) an orally consumed therapeutically effective amount of at least one required primary agent; (2) at least one required previously known medicament co-agent recognized as effective to treat a chronic inflammatory disease addressed herein administered to the mammalian subject via the oral route; and (3) one or more additional orally consumed required co-agent selected from the group consisting of antioxidants, vitamins, metabolites at risk of depletion, sulfhydryl co-agents, co-agents which may facilitate glutathione activity and nonabsorbable primary amine polymeric co-agents; so as to produce an additive or synergistic physiological effect of an anti-inflammatory nature.

12 Claims, No Drawings

COMPOSITIONS AND METHOD FOR TREATMENT OF CHRONIC INFLAMMATORY DISEASES

RELATED PATENT APPLICATIONS

This invention is a continuation-in-part of U.S. patent application Ser. No. 10/924,945, filed on Aug. 24, 2004 now abandoned, entitled "Compositions and Method for Treatment of Chronic Inflammatory Diseases,", which in turn is a continuation-in-part of U.S. patent application Ser. No. 09/610,073, filed on Jul. 5, 2000 now abandoned, entitled "Compositions and Method for Treatment of Chronic Inflammatory Diseases," which in turn is a continuation-in-part of U.S. patent application Ser. No. 08/814,291, filed on Mar. 10, 1997 now abandoned, entitled "Compositions and Method for Treatment of Chronic Inflammatory Diseases," which in turn is a continuation-in-part of U.S. patent application Ser. No. 08/241,603, filed on May 11, 1994 now abandoned, entitled "Compositions for Treatment of Chronic Inflammatory Diseases and Etiologically Related Symptomology," which is a continuation-in-part of U.S. patent application Ser. No. 07/906,909, filed on Jun. 30, 1992 now abandoned, entitled "Methods of Treating Chronic Inflammatory Diseases and Etiologically Related Symptomology Using Carbonyl Trapping Agents in Combination with Anti-Oxidants and Related Agents," the disclosure of which is incorporated by reference herein.

AIMS OF THE INVENTION

Accordingly, it is a general object of this invention to treat chronic inflammatory diseases by use of systemically administered compositions consisting of (a) a required primary agent which is an orally consumed carbonyl trapping substance selected from the closed group disclosed below, (b) at least one orally consumed required previously known medicament co-agent selected from the closed group disclosed below and which has been shown to or may contribute to the alleviation of symptomology of the diseases addressed herein, and (c) an additional orally consumed required co-agent selected from the group consisting of an antioxidant co-agent selected from the closed group disclosed below, a vitamin co-agent selected from the closed group disclosed below, a co-agent in the category of metabolites at risk of depletion selected from the closed group disclosed below, a sulfhydryl co-agent selected from the closed group disclosed below, a co-agent which may facilitate glutathione activity selected from the closed group disclosed below, and a non-absorbable primary amine polymeric co-agent selected from the closed group disclosed below; so as to create compositions with additive or synergistic physiological therapeutic characteristics and so as to overcome the disadvantages of the prior art. For purposes of the instant disclosure, systemic administration via the oral route is defined as meaning that a composition can be in the form of a powder, pills, capsules, tablets, lozenges, granules or an edible liquid containing the composition ingredients.

It is an object of the present invention that the required primary agents of the drug compositions originally described in U.S. patent application Ser. No. 07/906,909 can be combined with the required previously known medicament co-agents disclosed herein and the other required co-agents disclosed herein to treat chronic inflammatory diseases whose etiologies include the formation of toxic carbonyl compounds, said chronic inflammatory diseases being selected from the group consisting of chronic gingivitis; chronic periodontitis; chronic autoimmune gastritis; ileitis, including Crohn's disease; inflammatory bowel disease, including colitis; interstitial cystitis; psoriasis; forms of arthritis, including rheumatoid arthritis, ankylosing spondylitis and osteoarthritis; tendinitis or tenosynovitis; carpel tunnel syndrome and other cumulative trauma disorders; chronic discoid or systemic lupus erythematosus; pneumoconiosis due to inhalation of asbestos particles (asbestosis), inhalation of stone dust or quartz (silicosis) or inhalation of other causitive agents such as graphite, coal dust, particles produced by metal grinding, talc or corn dust; chronic obstructive pulmonary disease; inflammatory myopathies; inflammatory neuropathies; myasthenia gravis; multiple sclerosis; epilepsy; inflammatory site edema; post-event ischemia and reperfusion symptomology resulting from acute central nervous system trauma, including stroke and spinal cord trauma; post-event consequences of kidney ischemia and reperfusion; and post-event consequences of reperfusion subsequent to myocardial infarction. For the purposes of this disclosure, the aforementioned list of medical disorders shall constitute the closed class of chronic inflammatory diseases addressed herein.

It is another object of the present invention that in so far as the therapeutic procedures described herein may serve to delay the necessity of initiating the use of alternative medical procedures such as, for example, surgical operations or to decrease the dosages of known medicaments required to achieve beneficial effects, the period of prior art drug therapeutic value of the required previously known medicament co-agents may be extended and detrimental clinical side effects resulting from use of said required co-agent medicaments may be decreased, so that the overall effectiveness patient treatment may be improved.

It is a further object of this invention that use of the orally consumed required primary agents described herein in combination with the required previously known medicament co-agents and other required co-agents may be clinically applied so as to treat veterinary disorders comparable to at least some of those human disorders described above.

SUMMARY OF THE INVENTION

These and other objects of the present invention are achieved by providing a novel method for clinical treatment of chronic inflammatory diseases. The present invention involves, in part, use of orally administered amine derivatives of benzoic acid as carbonyl trapping agents as defined originally in U.S. patent application Ser. No. 07/906,909. These primary therapeutic agents act by chemically binding to and sequestering the aldehyde and/or ketone products of lipid peroxidation. Increased levels of lipid peroxidation have been repeatedly demonstrated as a part of the non-enzymatic "inflammatory cascade" process which underlies the secondary etiology of chronic inflammatory diseases. Furthermore, similar aldehyde products can be pathophysiologically generated at sites of inflammation by the action of myeloperoxidase in combination with hydrogen peroxide, chloride ions and α-amino acids.

p-Aminobenzoic acid (PABA) is an example of the primary absorbable pharmacological agent of the invention embodied in U.S. patent application Ser. No. 07/906,909. PABA has a small molecular weight, is water soluble, has a primary amine group capable of reacting with carbonyl-containing metabolites under physiological conditions and is tolerated by the body in relatively high dosages and for extended periods. The invention embodied in U.S. patent application Ser. No. 07/906,909 set forth the belief that carbonyl sequestering agents administered in oral dosages can be used in combination with co-agents consisting of proven antioxidant free radical trapping agents, and agents related thereto, so as to produce an additive or synergistic physiological effect of an anti-inflammatory nature. Co-agents of the invention embodied in U.S. patent application Ser. No. 07/906,909 include antioxidants (such as α-tocopherol), other vitamins, chemical conjugating agents which may facilitate kidney drug elimination (such as glycine), and orally administered nonabsorbable primary amine polymeric agents (such as chitosan).

These and other objects of the present invention will be apparent from the following detailed description.

DETAILED STATEMENT OF THE INVENTION

It is known that aldehyde chemical metabolites, which contain carbonyl functional groups, are generated by at least two distinct pathophysiological mechanisms during the process of chronic inflammation. In one of these pathophysiological mechanisms, aldehyde products result from increased lipid peroxidation, which may be initiated by a variety of activated oxygen chemical species such as the hydroxyl radical, HO. (Halliwell and Gutteridge, 1985, pp. 119-120). The reactive cascade of free radical propagation→lipid peroxidation→aldehyde formation and other subsequent effects of inflammation is well documented in the prior art (Halliwell and Gutteridge, 1985, pp. 102-103). The secondary carbonyl products of lipid peroxidation include saturated and unsaturated aldehydes, dialdehydes, epoxyaldehydes, lactones, furans, ketones and oxo acids (Merry and coworkers, 1991, pg. 362S). As reactive oxygen species are generated in vivo during states of limited oxygen availability, followed by reperfusion, a similar series of reactions takes place at sites of hypoxia/reperfusion injury (Demopoulos and coworkers, 1980; Dowling and coworkers, 1990, pg. 465). Aldehyde products of this reactive cascade are known to react with free amino groups of proteins, nucleic acids and phospholipids to form Schiff bases (Hatherill and coworkers, 1991, pg. 352). In a second pathophysiological mechanism, aldehyde products are generated at sites of inflammation by the action of myeloperoxidase in combination with hydrogen peroxide, chloride ions and α-amino acids (Hazen and coworkers, 1998).

Prior to submission of U.S. patent application Ser. No. 07/906,909, the methodological principle of using carbonyl-trapping agents to treat chronic inflammatory diseases was not recognized or disclosed.

Thus, the application of this principle in conjunction with use of known antioxidant free radical trapping agents to produce new and novel compositions which have improved therapeutic properties also was not recognized. When compared to previously disclosed understanding of the actions of recognized nonsteroidal anti-inflammatory drugs (Weissmann, 1991), it is evident that the inventive concept originally described in U.S. patent application Ser. No. 07/906,909 is novel.

Previously, attempts at pharmaceutical intervention in the nonenzymatic cascade of inflammatory reactions has focused primarily on use of both water-soluble and lipid-soluble antioxidant free radical trapping agents or use of metal chelating agents (Halliwell and Gutteridge, 1985, pp. 125 and 116-117). As iron and copper ions have been shown to induce hydroxyl radical formation (Halliwell and Gutteridge, 1985, pg. 123) and induce lipid peroxidation (Halliwell and Gutteridge, 1985, pg. 124), the use of metal chelating agents such as deferoxamine to ameliorate pathophysiological consequences of the non-enzymatic inflammatory cascade has received some attention (Halliwell and Gutteridge, 1985, pp. 116-117). However, deferoxamine has predictable ocular and auditory deleterious side effects (Halliwell and Gutteridge, 1985, pgs. 117 and 140), and prior examples of antioxidant free radical trapping agents and combinations thereof have proven to be of limited clinical value.

Both PABA and D-penicillamine are primary amine agents which also function as antioxidant free radical trapping agents. Yet as antioxidant agents PABA and D-penicillamine are presently regarded as being of secondary, nominal value, due either to weak antioxidant properties or toxic side effects, respectively. Thus their use as anti-inflammatory agents has been quite limited. Their potential value for trapping the aldehyde products of inflammation-related lipid peroxidation has never been recognized. Hence, the formulation of a new composition, such as one having PABA as its primary agent, an antioxidant as a required co-agent and at least one of the previously known medicament required co-agents disclosed herein intended for the treatment of a chronic inflammatory disease has never been recognized.

In considering the degree of novelty of this disclosure, one objective approach to this question is to examine the record of submission and review records of the U.S. Food and Drug Administration. In preparation for the submission of this disclosure, the present inventor consulted the web site at www.fda.gov. The present inventor typed in "PABA" in the FDA search box, and got 429 results. During the period from Feb. 8, 2008 to Feb. 14, 2008 the present inventor examined the entire FDA directory for PABA citations. In doing so, the present inventor found no citation that appears to anticipate any of the subject material contained within the metes and bounds of the instant disclosure. This point underscores the novelty of the instant disclosure, and its non-obviousness to those of ordinary skill in the art.

Further distinctions should be made between the invention of U.S. patent application Ser. No. 07/906,909 and previously recognized use of D-penicillamine, one of the "slow-acting" anti-inflammatory drugs mentioned in *Understanding Arthritis* (Kushner, 1984), a publication of the Arthritis Foundation. The primary amine primary agents described in the invention of U.S. patent application Ser. No. 07/906,909 are all derivatives of aminobenzoic acid, which should facilitate their safe elimination from the body by normal kidney filtration. D-Penicillamine is not a derivative of aminobenzoic acid. In addition, D-penicillamine has a reduced sulfhydryl group, unlike any of the primary agents claimed herein. However, D-penicillamine does have a primary amine functional group as well as a carboxylic acid functional group, like aminobenzoic acid. In *Understanding Arthritis* Kushner noted that:

Many doctors believe that the slow-acting drugs may slow the underlying disease, though how they do this is not clear. This group of drugs includes gold, penicillamine, cytotoxic, and antimalarial drugs. All of the drugs in this group have to be taken for many weeks, and often for several months, before their full effects become noticable. The relief they provide may last for some time after they are no longer being taken. But with these benefits of long-lasting relief and a possible slowing of the disease also comes a higher risk of serious side effects . . . (pages 55-56) . . . . Again, the side effects [of penicillamine] often require some people to stop taking this drug. Like gold, penicillamine may damage the kidneys and bone marrow, and may also cause fever, chills, rashes, sores in the mouth, a sore throat, stomach upset, muscle weakness, loss of taste, and easy bruising or bleeding. Because of these possible side effects, the drug is taken only with close supervision by a doctor . . . (page 57)

The invention embodied in U.S. patent application Ser. No. 07/906,909 constitutes an alternative slow-acting anti-inflammatory protocol that is believed to be inherently safer for the patient and to act via a mechanism not previously recognized or described. PABA is not among the antimalarial drugs discussed by Kushner (1984, pg. 57), nor is it among the antimalarial drugs listed in the Merck Index (Budavari and coworkers, 1989, pg. THER-16).

The invention embodied in U.S. patent application Ser. No. 07/906,909 is based on use of primary amine derivatives of benzoic acid as primary agents for chemically binding to and sequestering aldehyde products pathophysiologically generated at sites of inflammation, and their use in combination with previously recognized antioxidant free radical trapping co-agents. This unique, multiple-level approach to interference with certain steps in the non-enzymatic inflammatory cascade has not been previously disclosed. This is, in fact, the first anti-inflammatory agent invention that addresses the issue of aldehyde formation at inflammation sites. As aldehydes are highly reactive molecules capable of reacting with proteins, lipids and nucleic acids (Jellum and coworkers, 1973, pg. 200; Carden and coworkers, 1986), their increased formation at inflammation sites can be a significant contributing factor in the evolution of the clinical pathology of inflammatory disorders. Halliwell and Gutteridge (1985, pg. 123) noted that malonaldehyde . . . is only one of a great number of carbonyl compounds formed in peroxidising systems and often is only a tiny percentage of the total products formed . . . . Other toxic aldehydes include 4,5-dihydroxydecenal and 4-hydroxynonenal. Lipid peroxides and/or cytotoxic aldehydes derived from them can block macrophage action, inhibit protein synthesis, kill bacteria, inactivate enzymes, crosslink proteins and generate thrombin . . . .

The results of several published research studies suggest that dysfunctional lipid peroxidation may be a contributing factor in the etiology of a variety of chronic inflammatory diseases, such as rheumatoid arthritis (Jasin, 1993; Merry and coworkers, 1991; Panetta and coworkers, 1991; Rowley and coworkers, 1984), multiple sclerosis (Hunter and coworkers, 1985), silicosis (Katsnelson and coworkers, 1989, pg. 318), Duchenne muscular dystrophy (Kar and Pearson, 1979; Jackson and coworkers, 1984), colitis (Tamai and coworkers, 1992) and chronic inflammatory bowel disease (Ahnfelt-Ronne and coworkers, 1990). For the purposes of the present disclosure, the closed group of chronic inflammatory diseases addressed herein is defined as consisting of chronic gingivitis; chronic periodontitis; chronic autoimmune gastritis; ileitis, including Crohn's disease; inflammatory bowel disease, including colitis; interstitial cystitis; psoriasis; forms of arthritis, including rheumatoid arthritis, ankylosing spondylitis and osteoarthritis; tendinitis or tenosynovitis; carpel tunnel syndrome and other cumulative trauma disorders; chronic discoid or systemic lupus erythematosus; pneumoconiosis due to inhalation of asbestos particles (asbestosis), inhalation of stone dust or quartz (silicosis) or inhalation of other causitive agents such as graphite, coal dust, particles produced by metal grinding, talc or corn dust; chronic obstructive pulmonary disease; inflammatory myopathies; inflammatory neuropathies; myasthenia gravis; multiple sclerosis; epilepsy; inflammatory site edema; post-event ischemia and reperfusion symptomology resulting from acute central nervous system trauma, including stroke and spinal cord trauma; post-event consequences of kidney ischemia and reperfusion; and post-event consequences of reperfusion subsequent to myocardial infarction.

As exposure to asbestos fibers can stimulate lipid peroxidation (Halliwell and Gutteridge, 1985, pg. 152) and a chronic inflammatory response (Rom and coworkers, 1991, pg. 415), asbestosis is included as a disorder subject to treatment by practice of the present invention. Published evidence has also documented the generation of high free radical concentrations at the inflamed site of experimental foot pad edema (Dowling and coworkers, 1990, pg. 464), the ability of carbonyl compounds resulting from lipid peroxidation to induce foot edema in the rat (Benedetti and co-workers, 1980), and that formaldehyde is known to be an inflammatory and edematogenic agent (Wheeler-Aceto and Cowan, 1991). In addition, a role for reactive oxygen radicals has been proposed for numerous other disorders, including inflammatory vasculitis, emphysema, mineral dust pneumoconiosis and autoimmune nephrotic syndromes (Halliwell and Grootveld, 1987, pg. 10).

The study of Jasin (1993) provides a particularly good example of the role played by lipid peroxidation in chronic inflammatory disorders, this work focusing on oxidative damage to immunoglobulin G in synovial fluid derived from patients having rheumatoid arthritis. Patient Ig G samples described in this study featured evidence of oxidative damage and protein crosslinking, and smaller peptides present in these synovial samples exhibited evidence of high concentrations of thiobarbituric acid-reactive material. Jasin noted (pg. 168) that "these observations suggest that oxidative processes in inflammatory foci generate products derived from protein and lipids that may contribute to the self-perpetuation of inflammation." As noted by Dowling and coworkers (1990, pg. 464), Jasin's work represents a continuation of arthritic Ig G studies originally presented by Lunec and coworkers (1985).

Ischemia/reperfusion damage to various tissues appears to occur by a common mechanism, involving generation of free radicals and lipid peroxidation (Fleckenstein and coworkers, 1991). Increased lipid peroxidation has also been demonstrated in acute central nervous system trauma (Hall, 1987, pgs. 421 and 424; Demopoulos and co-workers, 1980, pgs. 97 and 112; Kontos and coworkers, 1981, pg. 2329), as a result of stroke (Zivin and Choi, 1991, pg. 61), subsequent to myocardial infarction (Kurdin, 1978) and in an experimental model of myocardial ischemia (Siminiak and Wysocki, 1992). Increased lipid peroxidation under such circumstances appears to be initiated by extravasation of blood, as iron-containing substances such as hematin catalytically accelerate lipid autoxidation (Demopoulos and coworkers, 1980, pgs. 97 and 115). Status epilepticus has also been linked to increased intracellular concentrations of free radicals, with subsequent lipid peroxidation (Del Maestro, 1980, pg. 163).

The inventive feature disclosed in U.S. patent application Ser. No. 07/906,909 is that compositions consisting of absorbable carbonyl trapping drugs in combination with known antioxidant free radical trapping co-agents and co-agents related thereto can be of particular benefit in preventing or ameliorating forms of chronic inflammation by incorporating two pharmacological strategies, the sequestering of cytotoxic aldehydes and ketones generated at sites of chronic inflammation and the sequestering of activated oxygen chemical species generated earlier in the non-enzymatic inflammatory cascade. It is further understood that oral use of nonabsorbable carbonyl trapping agents can serve to prevent absorption of dietary aldehydes and ketones from the alimentary tract into the body, thus complementing the intended therapeutic results.

The subject matter of the instant disclosure is that the information contained in U.S. patent application Ser. No.

07/906,909, as presently amended, is to be combined with the required use of one or more previously known medicaments selected from the closed group disclosed herein, so as to achieve still greater clinical benefit for some patients suffering from the presently addressed group of chronic inflammatory diseases.

(i) Mechanism of Action of Required Primary Agents

These pharmacological reactions are based on the ability of primary amine-containing substances to react with carbonyl functional groups of toxic substances, yielding covalently bound Schiff base products. Several examples of chemically analogous reactions, presented within other contexts, have been publicly presented. Representative examples are discussed below. These model chemical systems are directly analogous to the mechanism of drug action of the required primary agents of the present invention.

Comments by Feeney and coworkers (1975, pg. 141) provide an appropriate introduction to this subject:

A wide variety of substances with —NH$_2$ groups condense with carbonyl compounds . . . . This condensation of primary amines with aldehydes and ketones to give imines was first discovered by Schiff (1900). The overall equilibrium greatly favors hydrolysis in aqueous solution for aliphatic aldehydes. With aromatic aldehydes, the equilibrium is shifted in favor of Schiff base formation. It is important to note that increasing the nucleophilic strength of the amine will increase the rate of the carbonylamine reaction but will have almost no effect on the position of the equilibrium.

These comments suggest that the amine-containing carbonyl-trapping drugs described herein should have particular promise for binding furanaldehydes, which are aromatic. These comments also suggest that doses of absorbable amine drugs may require in vivo concentrations in the range of 1:100 to 1:1,000 (carbonyl:amine) in order to achieve clinical effectiveness. This, in turn, suggests that therapeutic dosages may lie in the range of grams per day and that only drugs of particularly low toxicity will have human applications.

Feeney and coworkers (1975, pg. 144) also noted the phenomenon of Schiff base transimination, which occurs to a significant extent at neutral pH:

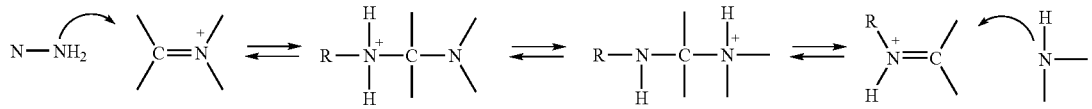

The existence of such non-enzymatic reversible transimination reactions is important within the context of this invention, as it suggests that in vivo both bound carbonyl agents, in addition to free carbonyl agents, may be sequestered by amine-containing drugs.

(a) The direct in vitro addition of p-aminobenzoic acid or ethyl p-aminobenzoate to malondialdehyde or its tautomer, β-hydroxyacrolein, has been described (Sawicki and coworkers, 1963).

(b) Self-polymerization of o-aminobenzaldehyde has been described. In the 1994 edition of the Sigma Chemical Company catalog of biochemical reagents the following statement appears on page 90 of its listing: "o-AMINOBENZALDEHYDE Unstable! [store at] −20° C. Polymerizes rapidly when exposed to room temperature. May yield slightly hazy solution in ethanol due to presence of a small amount of polymer. Shipped in dry ice." This information directly indicates that a primary amino group covalently linked to a benzene ring possesses sufficient reactivity for significant reaction with aldehyde functional groups at room temperature. It is apparent that no form of activation of the amino group is required and that a Schiff base product forms readily.

(c) The direct in vitro addition of n-hexylamine to β-hydroxyacrolein to produce an N,N'-disubstituted 1-amino-3-iminopropene derivative has been reported (Chio and Tappel, 1969). The reaction may be represented as follows:

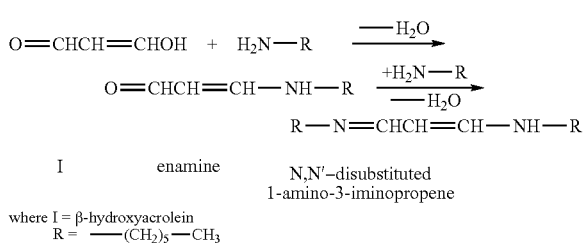

(d) The direct chemical addition of amines to 5-methyl-2-furfural has been described (Holdren and Hixon, 1946). A wide variety of aliphatic and aromatic primary amines can add to furfural in this manner, yielding Shiff base products (Dunlop and Peters, 1953, pg. 353).

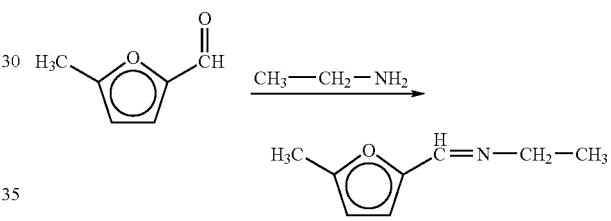

(e) As described by Dunlop and Peters (1953, pg. 373) earlier work demonstrated the ability of furfural to react with amino-sulfonic salts to produce furfurylideneaminosulfonates:

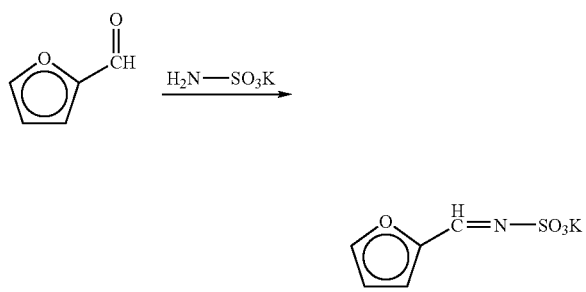

(f) The reaction of phenylaminoguanidine with furfural (Dunlop and Peters, 1953, pg. 371) serves as an example of covalent furanaldehyde trapping with a hydrazine:

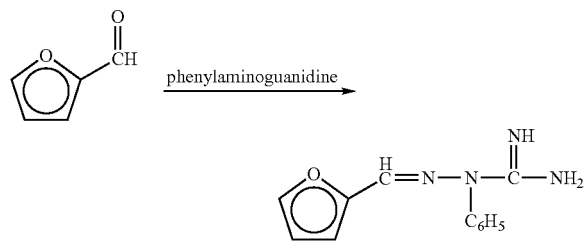

It is proposed that the orally administered, small molecular weight, absorbable, primary amine drugs described herein as the required primary agents of the instant disclosure will have analogous behavior in vivo. These primary agents also have an additional characteristic which will facilitate disposal as urine metabolites; all of these drugs contain a carboxylic acid group to facilitate uptake and processing by the kidneys.

The metabolic fate of PABA in humans has been actively investigated and well reported in the biomedical literature (Young and coworkers, 1971; Howie and Bourke, 1979). It is so actively metabolized via several mechanisms and quantitatively removed in urine (Bingham and Cummings, 1983; Weizman and coworkers, 1985) that PABA excretion has become a widely recognized standard for measuring urinary clearance. Small amounts of PABA are normally present in the human diet. It is recognized as being a vitamin for many organisms and is classified as a member of the vitamin B complex (Scott and Robbins, 1942; Winitz and coworkers, 1970, pgs. 527-528; Smith, 1976, pg. 194). As a vitamin for human use PABA is commercially marketed in the dosage range of 5 to 550 mg/day.

(ii) Examples of Required Primary Agents

The closed class of this category of primary agent is hereby limited to the following substances, each intended for systemic administration solely via the oral route. In addition to the free acid form of any carboxylic acid primary agent listed herein, the pharmaceutically acceptable salt forms, pharmaceutically acceptable ester derivatives, pharmaceutically acceptable amide derivatives and analogous pharmaceutically acceptable non-aromatic benzene ring derivative (i.e., cyclohexane carboxylic acid derivative) thereof are also useful. The class of primary agents (molecular weight range 100 to 1,400) of the present invention are limited to the chemical class structure listed below:

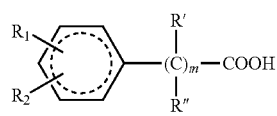

wherein $R_1$ is —$NH_2$; -aminoalkyl having 1-10 carbons; —NHC(=NH)$NH_2$; —$(CH_2)_n$NHC(=NH)$NH_2$ wherein n is 1-10; —C(=NH)$NH_2$; —$(CH_2)_n$—CH=NC(=NH)$NH_2$ wherein n is 1-10; —NHC(=NH)NHNH$_2$; —$(CH_2)_n$NHC(=NH)NHNH$_2$ wherein n is 1-10; —$(CH_2)_n$—CH=NC(=NH)NHNH$_2$ wherein n is 1-10; —NHNHC(=NH)$NH_2$; —$(CH_2)_n$—NHNHC(=NH)$NH_2$ wherein n is 1-10; and —$(CH_2)_n$—CH=N—NHC(=NH)$NH_2$ wherein n is 1-10;

$R_2$ is H; —OH; —O—$CH_3$; —O—R' wherein R' is alkyl of 2-10 carbons; aminoalkyl wherein the alkyl group is 1-10 carbons; —$SO_3H$; —$CH_3$; and —$(CH_2)_n$$CH_3$ wherein n is 1-10;

R' and R" are —H, —OH or —$CH_3$; and m is 0 or 1.

For purposes of this invention, a therapeutically effective amount of the required primary agent for a mammalian subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day.

By virtue of the size of each of these primary agents and the fact that each includes the benzoic acid moity within its chemical structure, each member of this closed class may reasonably be regarded as being readily absorbable from the gastrointestinal tract of the mammalian subject subsequent to oral consumption.

(iii) Mechanism of Action of Required Nonabsorbable Primary Amine Polymeric Co-Agents in a Microfibrillated Form or Microcrystalline Form The presence of aldehydes and ketones in the human diet may be a factor which may put a patient suffering from a chronic inflammatory disease further at risk. This might be especially important for victims of chronic autoimmune gastritis, ileitis and colitis, as the damaging effects of inflammation site carbonyl compounds may be accentuated by direct exposure to dietary carbonyl agents. 5-Methylfurfural has been identified in the oil of roasted coffee and in oil of cloves (Dunlop and Peters, 1953, pg. 403). 5-Hydroxy-methylfurfural has been found in sherry, port and brandy alcoholic beverages, honey and other sugar syrup products (Lever and co-workers, 1985). Levels of furfural (that is, 2-furanaldehyde or 2-furancarboxaldehyde) and 5-hydroxymethyl-2-furanaldehyde (that is, 5-hydroxymethylfurfural) as high as 4.5 mg/L and 93.2 mg/L, respectively, have been found in wine products (Shimizu and Watanabe, 1979). Furfural has also been detected in beer and distilled liquors (Dunlop and Peters, 1953, pg. 308), as well as in natural oil products such as oil of lime (Dunlop and Peters, 1953, pg. 280). Summarizing earlier work, Rice (1972) noted:

Small quantities of furfural occur in many foodstuffs, including—among many others—bread, coffee, processed fruits and fruit juices, and alcoholic beverages. In fact, whenever plant or animal tissue containing pentoses or hexoses is subjected to heat, the possibility arises that furfural, 5-hydroxymethyl furfural, and probably other furans as well will be produced.

Pettersen and Jellum (1972) referred to earlier work which demonstrated the generation of 2-furanaldehyde, 5-hydroxymethyl-2-furanaldehyde and 2,5-furandicarboxaldehyde during bread baking. In his food chemistry study, Baltes (1985) noted the presence of furfural in curing smoke tar; and the presence of furfural, 5-methyl-2-furfural, dihydrofuranone, 5-hydroxymethyl-2-furfural and 2,5-furandialdehyde in caramels. Baltes also examined the products obtained by Maillard reaction of glucose and phenylalanine and identified furfural and 2,5-di-(hydroxymethyl)-furan among the main components. Thus various furan aldehyde compounds have been identified in the human diet.

In addition, a wide variety of naturally occurring non-aromatic and aromatic aldehydes and ketones have been found in fruits and vegatables (Schauenstein and Esterbauer, 1977, pgs. 181-194). These include alkanals, alk-2,4-dienals, alk-2-enals, alk-1-en-3-ones, α-dicarbonyl compounds, β-dicarbonyl compounds and alkan-2-ones. Schauenstein and Estabauer have noted, in part, that:

Aliphatic carbonyl compounds represent the most important group of flavouring compounds in our foodstuffs. One finds them in all flavour extracts. They are either entirely, or in large measure, responsible for nearly all known flavours and determine, even when present in small amounts, the taste and odour of our foodstuffs, and beverages such as tea and coffee . . . (pg. 189)

As the presence of carbonyl agents in the diet is not restricted to fruits and vegatables, Schauenstein and Estabauer have further noted that:

Unsaturated aldehydes also arise through thermal degradation of carbohydrates, amino acids, and fats. Such thermal degradative processes are probably responsible for the presence of these aldehydes in boiled, fried, and baked foods. Unsaturated aldehydes have been detected in a large number of foodstuffs, such as potatoes, potato chips, poultry, meat, fish, salad oils, bread, and bakery products . . . (pgs. 193-194)

As such, it is apparent that the diet is a significant source of carbonyl agents, and their presence may be a contributing factor in the etiology of chronic inflammatory diseases. Toxic properties of furanaldehyde derivatives have been demonstrated in both in vivo and in vitro studies (Konecki and coworkers, 1974; Ulbricht and coworkers, 1984). The orally consumed nonabsorbable primary amine co-agents such as those defined below can be of health benefit by virtue of their ability to covalently trap dietary aldehydes and ketones. The co-agents described in this section can accomplish this function because they bear primary amine groups. As large molecular weight molecules which are non-digestible they have the capacity to pass through the digestive tract, acting in effect as another form of dietary fiber. These nonabsorbable polyamine trapping substances may be divided into three classes; naturally occurring polyamine polysaccharides, chemical derivatives of naturally occurring polysaccharides, and synthetic polyamine polymers.

The fate of malondialdehyde given orally to rats may serve as an example of the metabolism of dietary aldehydes, and how an understanding of this process can be used to define nonabsorbable carbonyl-trapping drugs. Studies by Draper and coworkers (1986) demonstrated that the primary form of "bound" MDA in rat or human urine is N-α-acetyl-ε-(2-propenal)lysine. This is the biologically acetylated derivative of the MDA-lysine adduct N-ε-(2-propenal)-lysine, as shown below.

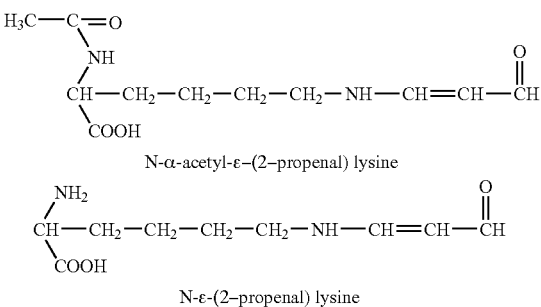

Draper and coworkers (1986) were able to generate N-ε-(2-propenal)-lysine in vitro by exposing beef muscle protein to MDA, followed by treatment with pepsin and hog intestinal juice. This indicates that the ε-amino groups of dietary protein lysine residues can covalently bind dietary aldehydes under conditions found in the intestinal tract. As such, chemically analogous primary amine groups on nonabsorbable polyamine co-agents of the present disclosure are capable of covalently binding dietary aldehydes under conditions to be found in the intestinal tract. In this case, however, the bound carbonyl species would be excreted in the feces, thus preventing subsequent in vivo exposure to dietary carbonyl agents.

In their study Draper and coworkers noted that N-α-acetyl-ε-(2-propenal)lysine was found in urine of fasted rats or animals fed on MDA-free diets, indicating that the MDA-lysine adduct also forms in vivo. These investigators referred to earlier work which demonstrated that the MDA concentration normally found in food is in the range of <0.1 to 10 ppm (<0.1 to 10 μM), which gives some idea of dietary aldehyde concentrations.

(iv) Closed Group of Required Nonabsorbable Polyamine Co-Agents
  in a microfibrillated form or microcrystalline form Useful in the Present Invention The closed group of this category of required co-agent is hereby limited to the following substances, each intended for systemic administration solely via the oral route. For purposes of this disclosure, a therapeutically effective amount of a required nonabsorbable polyamine co-agent for a mammalian subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day. Said a required co-agent may be prepared in a microfibrillated form or microcrystalline form having enhanced surface area, increased porosity, increased water retention capacity and enhanced chemical accessibility.

(a) Naturally Occurring Amine-Containing Polysaccharides

Any naturally occurring polysaccharide featuring β-1,2, β-1,3, β-1,4 and/or β-1,6 linkages which contains aminosugars may be regarded as a non-digestible, potentially active carbonyl trapping agent.

The chitin class of biopolymers may be cited as an example of such an agent, having the general structure of
  poly-β-(1→4)-N-acetyl-D-glucosamine A form of microcrystalline chitin has been described in which some of the acetyl groups have been removed, revealing free amine groups (Austin and coworkers, 1981, pg. 750). Chitins obtained from different sources feature different degrees of amine deacetylation (Austin and coworkers, 1981, pg. 752).

(b) Chemical Derivatives of Naturally Occurring Polysaccharides

Various pretreatment procedures may be applied to naturally occurring polysaccharides prior to generation of chemical derivatives. Generation of microcrystalline polysaccharides is one example of such a pretreatment procedure. As applied to cellulose or chitin (Yalpani, 1988, pg. 389), this yields a colloidal processed form of polysaccharide featuring high porosity and enhanced susceptibility to chemical reactions. Generation of "microfibrillated" cellulose or chitin is another example of a pretreatment procedure which produces enhanced surface area, increased water retention capacity and enhanced chemical accessibility (Yalpani, 1988, pg. 390). Use of strong (>18%) sodium hydroxide is still another recognized pretreatment, or activation, procedure found to be helpful as a starting point for preparing chemical derivatives of polysaccharides (Yalpani, 1988, pg. 214).

(b)(1) Deacetylation of Naturally Occurring Polysaccharides

A variety of polysaccharides have been identified which are rich in N-acetylated residues. Upon chemical deacetylation these carbohydrates yield high molecular weight derivatives bearing primary amine groups directly linked to sugar carbons, that is, no sidearm spacer units present.

i. Chitosan. This is the deacylated form of chitin. As described in the *Merck Index* (Budavari and coworkers, 1989, pg. 316) chitin is a cellulose-like biopolymer the composition of which consists mostly of N-acetyl-D-glucosamine residues covalvently linked by β-1,4 bonds. Chemical deacylation removes acetate, generating primary amine groups still covalently bound to the polysaccharide. Chitosan has recognized uses in water treatment, in photographic emulsions and in improving the dyability of synthetic fabrics and fibers. The free amine groups in this substance also give it chelating properties (Austin and coworkers, 1981).

ii. Chondroitin sulfate. This is a mucopolysaccharide found commonly in mammalian tissue. It consists of repeating disaccharide units, each of which has a D-glucuronic acid residue _1,4 linked to an N-acetylchondrosine residue (Budavari and coworkers, 1989, pg. 344).

iii. Hyaluronic acid. This mucopolysaccharide is also found commonly in mammalian tissues. It consists of glucuronic acid and glucosamine residues bound by β-1,3 and β-1,4 linkages (Budavari and coworkers, 1989, pp. 751-752).

iv. Keratan sulfate. This mammalian glycosaminoglycan consists of a repeating disaccharide unit of a C-6 sulfated C-2 N-acetylated sugar residue and a galactose residue linked by β-1,4 bonds (Yalpani, 1988, pp. 27-28).

(b)(2) Chemical Amination of Polysaccharides i. 2-Amino-2-deoxycellulose. Cellulose can be aminated by a process of selective oxidation, oximation and subsequent reduction with lithium aluminum hydride (Yalpani, 1988, pp. 281-282).

ii. Alternative amination procedures. Aminodeoxy polysaccharides can also be prepared via azide or hydrazide intermediates or by reductive amination using sodium cyanoborohydride (Yalpani, 1988, pg. 281). Besides being applied to cellulose, other non-digestible polysaccharides such as curdlan (Yalpani, 1988, pg. 22) can be aminated by such chemical procedures.

iii. 3-Aminopropylcellulose. Reaction of cyanoethylcellulose with borane-tetrahydrofuran or borane-dimethyl sulfide complexes in tetrahydrofuran generates 3-aminopropylcellulose (Yalpani, 1988, pgs. 250 and 255). In this derivative each primary amine group is at the end of a three-carbon sidearm.

iv. Aminoethylcellulose. This chemical has been previously marketed as an anion exchange column chromatography resin (Sigma Chemical Co. catalog, February 1981) and used as such in protein purification studies (Fasold, 1975, pp 481-482).

v. Other aminoalkyl-, amino(hydroxyalkyl)-, aminoalkyl-ether-, and amino(hydroxyalkyl)-ether-derivatives of cellulose, chitin and other naturally occurring non-digestible carbohydrates. Noting that the chemical methodology for producing such derivatives is documented in public domain literature, the biomedical application of such derivatives for therapeutic purposes described herein is also claimed. This would include:

aminoalkyl derivatives of the formula
$H_2N-(CH_2)_n$-[carbohydrate] where n=1-30, including alkyl isomers;

amino(hydroxyalkyl)-derivatives of the formula
$H_2N-(CH_2)_m-CHOH-(CH_2)_n$-[carbohydrate], where m=0-15 n=0-15;

aminoalkyl-ether-derivatives of the formula
$H_2N-(CH_2)_n-O$-[carbohydrate], where n=1-30; and amino(hydroxyakyl)-ether-derivatives of the formula
$H_2N-(CH_2)_m-CHOH-(CH_2)_n-O$-[carbohydrate], where m=0-15
n=0-15 vi. Aminobenzyl-derivatives of cellulose, chitin or other naturally occurring non-digestible carbohydrates. As the aromatic amine group is a weaker base than its aliphatic counterpart, this class of nonabsorbable amines should be less chemically active than amino- and aminoalkyl-derivatives described above. These derivatives are of the following general structures:

$H_2N-C_6H_4-(CH_2)_n$-[carbohydrate],
$H_2N-CH_2-C_6H_4-(CH_2)_n$-[carbohydrate],
$H_2N-C_6H_4-(CH_2)_n-O$-[carbohydrate] where n=0-30, and
$H_2N-C_6H_4-(CH_2)_m-CHOH-(CH_2)_n-O$-[carbohydrate] where m=0-15
n=0-15

This includes p-, o- and m-benzene ring amino- and aminomethyl-isomers, and alkyl group isomers.

vii. guanidine and aminoguanidine derivatives of cellulose, chitin or other naturally occurring nonabsorbable carbohydrates selected from the group consisting of:

$H_2N-C(=NH)$-[carbohydrate];

$H_2N-C(=NH)-(CH_2)_n$-[carbohydrate], where n=1-10, including hydrocarbon isomers and hydroxylated derivatives thereof;

$H_2N-C(=NH)-O-(CH_2)_n$-[carbohydrate], where n=1-10, including hydrocarbon isomers, ether linkage isomers and hydroxylated derivatives thereof;

$H_2N-C(=NH)-NH$-[carbohydrate];

$H_2N-C(=NH)-NH-(CH_2)_n$-[carbohydrate], where n=1-10, including hydrocarbon isomers and hydroxylated derivatives thereof;

$H_2N-C(=NH)-NH-(CH_2)_n-O$-[carbohydrate], where n=1-10, including hydrocarbon isomers, ether linkage isomers and hydroxylated derivatives thereof;

$H_2N-C(=NH)-N=CH-(CH_2)_n$-[carbohydrate], where n=1-10, including hydrocarbon isomers and hydroxylated derivatives thereof;

$H_2N-C(=NH)-N=CH-(CH_2)_n-O$-[carbohydrate], where n=1-10, including hydrocarbon isomers and hydroxylated derivatives thereof;

$H_2N-NHC(=NH)-NH$-[carbohydrate];

$H_2N-NHC(=NH)-NH-(CH_2)_n$-[carbohydrate], where n=1-10, including hydrocarbon isomers and hydroxylated derivatives thereof;

$H_2N-NHC(=NH)-NH-(CH_2)_n-O$-[carbohydrate], where n=1-10, including hydrocarbon isomers, ether linkage isomers and hydroxylated derivatives thereof;

$H_2N-NHC(=NH)-N=CH-(CH_2)_n$-[carbohydrate], where n=1-10, including hydrocarbon isomers and hydroxylated derivatives thereof;

$H_2N-NHC(=NH)-N=CH-(CH_2)_n-O$-[carbohydrate], where n=1-10, including hydrocarbon isomers, ether linkage isomers and hydroxylated derivatives thereof;

$H_2N-C(=NH)-NH-NH$-[carbohydrate];

$H_2N-C(=NH)-NH-NH-(CH_2)_n$-[carbohydrate], where n=1-10, including hydrocarbon isomers and hydroxylated derivatives thereof;

$H_2N-C(=NH)-NH-NH-(CH_2)_n-O$-[carbohydrate], where n=1-10, including hydrocarbon isomers, ether linkage isomers and hydroxylated derivatives thereof;

$H_2N-C(=NH)-NH-N=CH-(CH_2)_n$-[carbohydrate], where n=1-10, including hydrocarbon isomers and hydroxylated derivatives thereof;

$H_2N-C(=NH)-NH-N=CH-(CH_2)_n-O$-[carbohydrate], where n=1-10, including hydrocarbon isomers, ether linkage isomers and hydroxylated derivatives thereof;

(b)(3) Aminated Sucrose Polyesters

Mixtures of fatty acid hexa-, hepta- and octaesters of sucrose, known as sucrose polyester, are not hydrolyzed by pancreatic lipase enzymes and are not absorbed in the intestine (Jandacek, 1984). It is disclosed and claimed herein that primary amine, aminoguanidine and guanidine derivatives of sucrose polyesters are of benefit in reduction of dietary carbonyl substances, analogous to the proposed action of other nonabsorbable agents described herein. Such derivatives of sucrose polyesters would include structures in which the carbonyl trapping functional group is in the ω-, ω-1 or other isomeric position(s) within the fatty acyl chains, fatty acyl chains having more than one nitrogen functional group and fatty acyl chains having hydroxyl groups. Such aminated sucrose polyesters may be used in pure form as a dietary supplement, or may be prepared as a coating on a particulate carrier such as, for example, cellulose or styrene divinylbenzene copolymer resin.

(c) Synthetic Polyamine Polymers (c)(1) Synthetic polysaccharides consisting partly or entirely of aminosugars bound by β-1,2, β-1,3, β-1,4 and/or β-1,6 linkages may be regarded as nonabsorbable carbonyl trapping agents.

(c)(2) Mixed polysaccharide polymeric derivatives. Primary amine, aminoalkyl (one to ten carbons per alkyl group), amino-hydroxyalkyl (one to ten carbons per alkyl group and one to ten hydroxyl groups per alkyl group), aminoguanidine, aminoguanidinyl-alkyl (one to ten carbons per alkyl group), aminoalkylguanidinyl (one to ten carbons per alkyl group), guanidine, aminobenzene and aminoalkylbenzene (one to ten carbons per alkyl group) functional groups may be covalently attached to matrices such as, for example, epi-chlorohydrin copolymers of cellulose or chitin. Functional group spacer groups may include alkene as well as alkyl groups.

(c)(3) Non-polysaccharide polymeric derivatives. Primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and aminoalkylbenzene (one to ten carbons per alkyl group) functional groups may be covalently attached to a wide variety of synthetic non-digestible polymers. Functional group spacer groups may include alkene as well as alkyl groups. Like their sugar-based counterparts, these agents should be capable of reacting with dietary carbonyl compounds. Nitrogen-containing functional groups may be covalently attached to synthetic supports such as, for example, polystyrene, styrene-divinylbenzene copolymer, polyvinyl alcohol and crosslinked derivatives thereof.

(v) Co-Administration of Required Antioxidant Co-Agents Selected from the Following Closed Group As regards the use of required orally consumed antioxidant co-agents, required orally consumed vitamin co-agents, required orally consumed co-agents which are metabolites at risk of depletion, required orally consumed sulfhydryl co-agents and required orally consumed co-agents which may facilitate glutathione activity, it is assumed herein that dosage ranges for these co-agents refer to adult human use and may be adjusted accordingly for use by children or by other mammals on a per kilogram basis.

The closed group of required antioxidant co-agents is hereby limited to the following substances, each intended for systemic administration solely via the oral route. It is claimed herein that the therapeutic value of the primary agents of the instant disclosure c a n be maximized by administration in conjunction with recognized antioxidant co-agents, including free radical trapping substances and substances that inhibit lipid peroxidation, such as α-tocopherol (Ferrari and coworkers, 1991, pg. 97S; Stuckey, 1968, pp. 214-215), dosage range from 100 I. U. daily to 3,500 I. U. daily. This dosage range for a-tocopherol is also claimed for other vitamin E derivatives such as β-tocopherol, γ-tocopherol, δ-tocopherol, ε-tocopherol, $\zeta_1$-tocopherol, $\zeta_2$-tocopherol and η-tocopherol, as well as pharmaceutically acceptable ester derivatives thereof such as the corresponding acetate, succinate and nicotinate forms.

Citric acid, dosage range from 200 mg daily to 20 gm daily, is included in this category of co-agents, as it is recognized as having antioxidant properties (*Merck Index*, Budavari, 1989, pg. 363). Alternatively, this co-agent may be consumed as a combination of potassium citrate monohydrate and citric acid monohydrate in a weight ratio of 3.3 to 1, or other weight ratio selected so as to alkalinize a composition. Citric acid is also recognized as an inhibitor of Maillard reactions (Stuckey, 1968, pg. 210).

In a published list of agents which function to supplement the chain-breaking antioxidant property of vitamin E, Tappel (1970, pg. 1138) included ubiquinol and seleno-amino acids. An oral dosage range from 10 mg daily to 500 mg daily for the class of ubiquinols, coenzyme $Q_n$ where n=1-12, is proposed herein. L-Selenocysteine, dosage range from 200 mg daily to 4 gm daily, is included in this co-agent category. L-Selenomethionine, dosage range from 200 mg daily to 4 gm daily, is also included in this co-agent category.

Other substances in this closed co-agent group include butylated-hydroxytoluene (Frankel, 1987, pg. 81), dosage range from 10 mg daily to 1 gm daily; butylated hydroxyanisole (Sies, 1991, pg. 32S), dosage range from 5 mg daily to 40 mg daily; propyl gallate (Verhagen and coworkers, 1991, pg. 113), dosage range from 10 mg daily to 1 gm daily; dodecyl-gallate (Verhagen and coworkers, 1991, pg. 113), dosage range from 10 mg daily to 1 gm daily; tertbutylhydroquinone (Verhagen and coworkers, 1991, pg. 113), dosage range from 10 mg daily to 1 gm daily; dihydrolipoic acid (Sies, 1991, pgs. 33S and 36S), dosage range from 10 mg daily to 4 gm daily; prostaglandin $B_1$ oligomers (also known as polymeric 15-keto prostaglandin B or $PGB_x$), dosage range from 5 mg/kg daily to 400 mg/kg daily; 2-aminomethyl-4-tert-butyl-6-iodophenol, dosage range from 0.5 mg/kg daily to 600 mg/kg daily (Swingle and coworkers, 1985, pg. 120); 2-aminomethyl-4-tert-butyl-6-propionylphenol, dosage range from 20 mg/kg daily to 500 mg/kg daily (Swingle and coworkers, 1985, pgs. 120-121); 2,6-di-tert-butyl-4-[2'-thenoyl]phenol, dosage range from 3 mg/kg daily to 300 mg/kg daily (Swingle and coworkers, 1985, pg. 121); N,N'-diphenyl-p-phenylenediamine, dosage range from 5 mg/kg daily to 500 mg/kg daily (Swingle and coworkers, 1985, pg. 118); ethoxyquin, dosage range from 5 mg/kg daily to 500 mg/kg daily (Swingle and coworkers, 1985, pg. 118); probucol, a synthetic antioxidant (Halliwell, 1991, pg. 586), dosage range from 25 mg daily to 1 gm daily; ebselen, dosage range from 5 mg/kg daily to 500 mg/kg daily; 5-[[3,5-bis(1,1-dimethylethyl)-4-hydroxyphenyl]methylene]-3-(dimethylamino)-4-thiazolidinone (LY221068; Panetta and coworkers, 1991), dosage range from 1 mg/kg daily to 100 mg/kg daily; 5-[[3,5-bis(1,1-dimethylethyl)-4-hydroxyphenyl]methylene]-3-(methylamino)-4-thiazolidinone (LY269415, Panetta and coworkers, 1991), dosage range from 1 mg/kg daily to 100 mg/kg daily; D-myoinositol-1.2.6-trisphosphate (Claxson and coworkers, 1990), dosage range from 10 mg/kg daily to 1.5 gm/kg daily; nordihydroguaiaretic acid, dosage range from 100 mg/kg daily to 2 gm/kg daily; deferoxamine mesylate, dosage range from 100 mg daily to 2 gm daily; tirilazad mesylate (U-74006F), dosage range from 150 μg/kg/hr to 15 mg/kg/hr; derivative of tirilazad in which the steroid portion of the chemical structure has been replaced with the tetramethyl chroman portion of d-α tocopherol (U78517F, Upjohn), dosage range from 150 µg/kg/hr to 15 mg/kg/hr; trimetazidine, dosage range from 100 µg/kg daily to 3.0 mg/kg daily; N,N'-dimethylthiourea (Repine, 1991), dosage range from 5 mg/kg daily to 100 mg/kg daily; zinc carnosine (Mahmood, 2007), dosage range from 70 µg/kg to 10 mg/kg daily; and 2-(2-hydroxy-4-methylphenyl)aminothiazole hydrochloride (Bonne and coworkers, 1990), dosage range from 0.1 mg/kg daily to 50 mg/kg daily. Selenium is also included in this group, dosage range from 25 µg daily to 0.5 mg daily, as it has recognized indirect antioxidant properties (Stuckey, 1968, µg. 236). Some in vivo experimental data has been presented which indicates that α-tocopherol; butylated-hydroxytoluene; propyl gallate; 2-aminomethyl-4-tert-butyl-6-iodophenol; 2-aminomethyl-4-tert-butyl-6-propionylphenol; 2,6-di-tert-butyl-4-[2'-thenoyl]-phenol; N,N'-diphenyl-p-phenylenediamine; ethoxyquin; ebselen; 5-[[3,5-bis(1,1-dimethylethyl)-4-hydroxyphenyl]methylene]-3-(dimethylamino)-4-thiazolidinone; 5-[[3,5-bis(1,1-dimethylethyl)-4-hydroxyphenyl]-methylene]-3-(methylamino)-4-thiazolidinone; nordihydroguaiaretic acid; 2-(2-hydroxy-4-methylphenyl)aminothiazole hydrochloride; and D-myoinositol-1.2.6-trisphosphate possess both anti-inflammatory and antioxidant properties (Swingle and coworkers, 1985, pgs. 114, and 118-121; Claxson and coworkers, 1990; Schmidt and Bayer, 1990, pg. 149; Honkanen and coworkers, 1990, pg. 190; Gado and Gigler, 1991; Panetta and coworkers, 1991; Parnham and coworkers, 1991).

For purposes of the present invention, the following substances are also included in the closed group of required antioxidant co-agents: aspirin, dosage range from 300 mg daily to 6.5 gm daily; potassium salicylate, dosage range from 300 mg daily to 6.5 gm daily; calcium acetylsalicylate, dosage range from 300 mg daily to 6.5 gm daily; choline salicylate, dosage range from 500 mg daily to 4 gm daily; imidazole salicylate, dosage range from 50 µmol/kg daily to 0.5 mmol/kg daily; choline magnesium trisalicylate (Trilisate, Purdue Frederick), dosage range from 500 mg daily to 4 gm daily; magnesium salicylate, dosage range from 500 mg daily to 4 gm daily; and salsalate, (Salflex, Carnrick Laboratories), dosage range from 500 mg daily to 4 gm daily.

Additional members of the closed group of required antioxidant co-agents disclosed and claimed within the metes and bounds of this invention also include the following substances, each having initially been recognized as a plant (e.g., vegetable) antioxidant and/or free radical trapping active ingredient. This category includes parthenolide, dosage range from 10 mg daily to 1 gm daily; daidzin, dosage range from 10 mg daily to 1 gm daily; genistein, dosage range from 10 mg daily to 1 gm daily; quercetin, dosage range from 10 mg daily to 1 gm daily; morin, dosage range from 10 mg daily to 1 gm daily; curcumin, dosage range from 10 mg daily to 1 gm daily; apigenin, dosage range from 10 mg daily to 1 gm daily; sesamol, dosage range from 10 mg daily to 1 gm daily; chlorogenic acid, dosage range from 10 mg daily to 1 gm daily; fisetin, dosage range from 10 mg daily to 1 gm daily; ellagic acid, dosage range from 10 mg daily to 1 gm daily; quillaia saponin, dosage range from 10 mg daily to 1 gm daily; capsaicin, dosage range from 10 mg daily to 1 gm daily; ginsenoside, dosage range from 10 mg daily to 1 gm daily; silymarin, dosage range from 10 mg daily to 1 gm daily; kaempferol, dosage range from 10 mg daily to 1 gm daily; ginkgetin, dosage range from 10 mg daily to 1 gm daily; bilobetin, dosage range from 10 mg daily to 1 gm daily; isoginkgetin, dosage range from 10 mg daily to 1 gm daily; isorhamnetin, dosage range from 10 mg daily to 1 gm daily; herbimycin, dosage range from 10 mg daily to 1 gm daily; rutin, dosage range from 10 mg daily to 1 gm daily; bromelain, dosage range from 10 mg daily to 1 gm daily; levendustin A, dosage range from 10 mg daily to 1 gm daily; and erbstatin, dosage range from 10 mg daily to 1 gm daily.

For the purposes of this invention, dimethyl sulfoxide is exempted from inclusion in this category of co-agent or any other category of co-agent herein. Likewise, for the purposes of this invention, ascorbic acid, also known as vitamin C, or any pharmaceutically acceptable derivative thereof is also exempted from inclusion in this category of co-agent or any other category of co-agent herein.

(vi) Closed Group of Required Vitamin Co-Agents

The closed group of this category of required co-agent is hereby limited to the following substances, each intended for systemic administration solely via the oral route. It is yet still another aspect of this invention that the safety and effectiveness of the products described herein may be optimized by prophylactic co-administration of vitamins which may be inadvertently depleted by the treatment or which may otherwise contribute to the clinical effectiveness of the compositions. This group includes:

retinol, dosage range from 10 µg/kg daily to 1 mg/kg daily;
vitamin A aldehyde (retinal), dosage range from 10 µg/kg daily to 1 mg/kg daily;
vitamin A acid (retinoic acid), dosage range from 10 µg/kg daily to 1 mg/kg daily;
retinyl acetate, dosage range from 10 µg/kg daily to 1 mg/kg daily;
vitamin $B_1$ (thiamine HCl), dosage range from 1 mg daily to 1.5 gm daily;
thiamine propyl disulfide, dosage range from 1 mg daily to 1.5 gm daily;
thiamine disulfide, dosage range from 1 mg daily to 1.5 gm daily;
thiamine disulfide O,O-diisobutyrate, dosage range from 1 mg daily to 1.5 gm daily;
thiamine disulfide hydrochloride, dosage range from 1 mg daily to 1.5 gm daily;
disulfide phosphate, dosage range from 1 mg daily to 1.5 gm daily;
thiamine mononitrate, dosage range from 1 mg daily to 1.5 gm daily;
thiamine 1,5-salt, dosage range from 1 mg daily to 1.5 gm daily;
phosphoric acid ester chloride, dosage range from 1 mg daily to 1.5 gm daily;
thiamine phosphoric acid ester phosphate salt, dosage range from 1 mg daily to 1.5 gm daily;
thiamine triphosphoric acid ester, dosage range from 1 mg daily to 1.5 gm daily;
benfotiamine (vitamin $B_1$ source), dosage range from 1 mg daily to 1.5 gm daily;
vitamin $B_2$ (riboflavin), dosage range from 1 mg daily to 1 gm daily;
riboflavin tetrabutyrate, dosage range from 1 mg daily to 1 gm daily;
riboflavine 5'-phosphate ester monosodium salt, dosage range from 1 mg daily to 1 gm daily;
vitamin $B_6$ (pyridoxine HCl), dosage range from 10 mg daily to 1.75 gm daily;
pyridoxal, dosage range from 10 mg daily to 1.75 gm daily;
pyridoxal HCl, dosage range from 10 mg daily to 1.75 gm daily;
pyridoxal 5-phosphate, dosage range from 10 mg daily to 1.75 gm daily;
pyridoxal 5-phosphate calcium salt, dosage range from 10 mg daily to 1.75 gm daily;

pyridoxamine, dosage range from 10 mg daily to 1.75 gm daily;

pyridoxamine dihydrochloride, dosage range from 10 mg daily to 1.75 gm daily;

pyridoxamine phosphate, dosage range from 10 mg daily to 1.75 gm daily;

vitamin $B_{12}$ (cyanocobalamin), dosage range from 1 μg daily to 1 mg daily;

methyl vitamin $B_{12}$ (co-methylcobalamin), oral dosage range from 1 μg daily to 1 mg daily;

vitamin $D_2$, dosage range from 400 units daily to 40,000 units daily;

vitamin $D_3$, dosage range from 400 units daily to 40,000 units daily;

vitamin $D_4$, dosage range from 400 units daily to 40,000 units daily;

vitamin H (biotin), dosage range from 150 μg daily to 200 mg daily;

vitamin $K_1$ (phytonadione), dosage range from 100 μg daily to 100 mg daily;

diacetyl dihydro vitamin $K_1$, dosage range from 100 μg daily to 100 mg daily;

vitamin $K_1$ oxide, dosage range from 100 μg daily to 100 mg daily;

vitamin(s) $K_2$ (menaquinones), dosage range from 100 μg daily to 100 mg;

vitamin $K_{2(35)}$, dosage range from 100 μg daily 100 mg daily;

vitamin $K_{2(35)}$ dihydrodiacetate, dosage range from 100 μg daily to 100 mg daily;

vitamin $K_{2(30)}$, dosage range from 100 μg daily to 100 mg daily;

vitamin $K_{2(30)}$ dihydrodiacetate, dosage range from 100 μg daily to 100 mg daily;

vitamin $K_5$, dosage range from 100 μg daily to 100 mg daily;

vitamin $K_5$ hydrochloride, dosage range from 100 μg daily to 100 mg daily;

N-acetyl vitamin $K_5$, dosage range from 100 μg daily to 100 mg daily;

vitamin $K_6$, dosage range from 100 μg daily to 100 mg daily;

vitamin $K_6$ dihydrochloride, dosage range from 100 μg daily to 100 mg daily;

vitamin $K_7$, dosage range from 100 μg daily to 100 mg daily;

vitamin $K_7$ hydrochloride, dosage range from 100 μg daily to 100 mg daily;

vitamin K-S(II), dosage range from 100 μg daily to 100 mg daily;

vitamin $L_1$, dosage range from 10 mg daily to 500 mg daily;

vitamin $L_2$, dosage range from 10 mg daily to 500 mg daily;

vitamin U, dosage range from 25 mg daily to 1 gm daily;

methylmethioninesulfonium bromide (bromide analog of vitamin U, dosage range from 25 mg daily to 1 gm daily;

α-carotene, dosage range from 20 mg daily to 300 mg daily;

β-carotene, dosage range from 20 mg daily to 300 mg daily;

γ-carotene, dosage range from 20 mg daily to 300 mg daily;

ω-carotene, dosage range from 20 mg daily to 300 mg daily;

ψ-,ψ-carotene (also known as lycopene; Sies, 1991, pg. 33S), dosage range from 5 mg daily to 1 gm daily;

7,7',8,8',11,12-hexahydro-ψ-,ψ-carotene (also known as phytofluene; Halliwell, 1991, pg. 576), dosage range from 5 mg daily to 300 mg daily;

L-carnitine (vitamin $B_T$; Carnitor, Sigma-Tau Pharmaceuticals), dosage range from 100 mg daily to 3 gm daily;

acetyl-L-carnitine, dosage range from 100 mg daily to 3 gm daily;

folic acid (vitamin Bc), dosage range from 0.5 mg daily to 50 mg daily;

folinic acid, dosage range from 0.5 mg daily to 50 mg daily;

folinic acid calcium salt pentahydrate, dosage range from 0.5 mg daily to 50 mg daily;

niacinamide, dosage range from 100 mg daily to 10 gm daily;

nicotinic acid (vitamin $B_3$; Nicolar, Rhone-Poulenc Rorer), dosage range from 100 mg daily to 10 gm daily;

nicotinic acid sodium salt sesquihydrate, dosage range from 100 mg daily to 10 gm daily;

nicotinic acid monoethanolamine salt, dosage range from 100 mg daily to 10 gm daily;

creatine, dosage range from 100 mg daily to 10 gm daily;

creatine monohydrate, dosage range from 100 mg daily to 10 gm daily; and guanidinoacetic acid, dosage range from 100 mg daily to 10 gm daily.

Several of these vitamins possess carbonyl functional groups and thus may be depleted by clinical use of the present invention. Others have a reported antioxidant effect, such as the carotenes, or may possess an anti-inflammatory effect, such as carnitine (Elliott and coworkers, 1991), retinoic acid (Fumarulo and coworkers, 1991) and retinyl acetate (Fumarulo and coworkers, 1991).

(vii) Closed Group of Required Co-Agents in the Category of Metabolites at Risk of Depletion The closed group of this category of required co-agent is hereby limited to the following substances, each intended for systemic administration solely via the oral route. It is another aspect of this invention that the safety and effectiveness of the compositions disclosed herein may be optimized by co-administration of other metabolites, such as glycine, which may be depleted within the body during long term drug use. Use of glycine within the dosage range of from 1 gm daily to 20 gm daily is claimed herein. As many of the primary agents of the instant disclosure are excreted from the body as glycine conjugates, co-administration of glycine may be advisable. Coenzyme A is a required cofactor for hippuricase, the liver enzyme which adds glycine to benzoic acid derivatives. Activity of hippuricase in glycinating some of the absorbable carbonyl-trapping drugs described herein may sequester a disproportionate fraction of the endogenous coenzyme A pool. Hence co-administration of pantothenic acid, a metabolic precursor of coenzyme A, may also serve to optimize the therapeutic procedures described herein. A dosage range of from 5 mg daily to 2 gm daily for pantothenic acid is claimed herein. Likewise, a dosage range of from 5 mg daily to 2 gm daily for use of the pharmaceutically acceptable salt forms of pantothenic acid, such as pantothenic acid sodium salt or pantothenic acid calcium salt, is also claimed herein.

(viii) Closed Group of Required Sulfhydryl Co-Agents

The closed group of this category of required co-agent is hereby limited to the following substances, each intended for systemic administration solely via the oral route. In a published list of agents that function to supplement the chain-breaking antioxidant property of vitamin E, Tappel (1970, pg. 1138) included sulfhydryl compounds such as glutathione, L-cysteine and L-methionine. A dosage range from 10 mg daily to 5 gm daily for glutathione is proposed herein. Noting the well documented ability of carbonyl agents to react with sulfhydryl groups (Jellum and coworkers, 1973), L-methionine, dosage range from 200 mg daily to 4 gm daily, and homocysteine, dosage range from 200 mg daily to 2 gm daily, are disclosed herein as useful co-agents of this category. Homocysteine contains a free sulfhydryl group. Likewise, acetyl-homocysteine thiolactone, dosage range from 0.5 mg/kg daily to 25 mg/kg daily, is also included in this co-agent group. L-Methionine is converted in vivo to homocysteine by several enzymatic reactions which remove a methyl group. L-Methionine also has a demonstrated ability to scavenge hypochlorous acid, a reactive oxygen specie which may contribute to the degradation of hyaluronic acid seen in rheumatoid arthritis (Saari and coworkers, 1993, pgs. 404 and 408). Cysteine, dosage range from 200 mg daily to 4 gm daily, is included in this co-agent category. Thioctic acid, also known as α-lipoic acid, is also included in this co-agent category in a dosage range from 10 mg daily to 4 gm daily, including its pharmaceutically acceptable sodium salt and ethylenediamine derivatives, as its structure includes a disulfide group. This agent, a recognized growth factor (Budavari and coworkers, 1989, pg. 1469), may tend to be depleted in the tissues of patients having chronic inflammatory diseases involving etiologies that include dysfunction of aldehyde and/or ketone metabolism. The ability of acetaldehyde to combine with thioctic acid, thus deactivating it, has been reported (Smith, 1976, pg. 195).

(ix) Closed Group of Required Co-Agents Which May Facilitate Glutathione Activity In addition, the present invention includes use of various required co-agents which may facilitate glutathione activity. The closed group of this category of optional co-agent is hereby limited to the following substances, each intended for systemic administration solely via the oral route. Use of N-acetylcysteine (Dansette and coworkers, 1990), dosage range from 10 mg/kg daily to 150 mg/kg daily, has been reported to increase the levels of plasma cysteine, plasma glutathione and red blood cell glutathione (Bernard, 1991), and to induce a 100-fold increase in myocardial glutathione subsequent to experimental ischemia and reperfusion (Ferrari and coworkers, 1991). N-Acetylcysteine reacts with hypochlorous acid, $HO^-$ and $H_2O_2$ (Bernard, 1991), as well as with reactive aldehydes found in tobacco smoke (Ohman and coworkers, 1992). Other substances in this class include L-2-oxothiazolidine-4-carboxylic acid, reported to hydrolyse in vivo to cysteine (Halliwell, 1991, pg. 590), dosage range from 0.3 mmol/kg daily to 3 mmol/kg daily; timonacic, also known as 4-thiazolidinecarboxylic acid (Dansette and coworkers, 1990), dosage range from 10 mg daily to 500 mg daily; cysteamine (Dansette and coworkers, 1990), dosage range from 200 mg daily to 4 gm daily; lipoamide derivatives (Dansette and coworkers, 1990) such as malotilate (Kantec), dosage range from 100 mg daily to 2 gm daily; sularlem (ADT; Dansette and coworkers, 1990), dosage range from 100 mg/kg daily to 1 gm/kg daily; and oltipraz (Dansette and coworkers, 1990), dosage range from 100 mg/kg daily to 1 gm/kg daily, as these co-agents may further serve to improve upon the invention described in U.S. patent application Ser. No. 07/906,909.

(x) Co-Administration of Required Previously Known Medicament Co-Agents as Selected from the Following Closed Group The closed group of this category of systemically administered required co-agent is hereby limited to the following substances, each administered solely via the oral route. For each member of this closed class, its preferred daily dosage range is illustrated below in Section (xiv). For any of member of this class of required co-agent, the preferred dosage range for an adult human subject is stated in the examples presented below. The substances included within this closed group are limited to: penicillin G potassium, penicillin G benzathine and penicillin G procaine combination, penicillin V potassium, erythromycin, amoxicillin, amoxicillin in combination with clavulanate potassium, tetracycline, doxycycline, minocycline, metronidazole, chlorhexidine gluconate, triclosan, sanguinarine, alclometasone 17,21-dipropionate, betamethasone, betamethasone 17,21-dipropionate, betamethasone valerate, cortisone, dexamethasone, fluocinolone acetonide, fluticasone propionate, hydrocortisone, hydrocortisone acetate, methylprednisolone, methylprednisolone acetate, mometasone 17-(2-furoate), prednisolone, prednisone, suprofen, triamcinolone, triamcinolone acetonide, triamcinolone diacetate, sulfasalazine, sodium guaiazulene-3-sulfonate, metronidazole, deodorized opium tincture, codeine, cyclosporin A, zileuton, corticotropin, biperiden, biperiden lactate, propantheline bromide, clobetasol propionate, methoxsalen, etretinate, clidanac, isotretinoin, anthralin, vitamin $D_3$, diclofenac, aceclofenac, felbinac, fenclorac, etodolac, fenclofenac, ketorolac, lonazolac-Ca, amfenac, isoxepac, isofezolac, ibufenac, sulindac, aloxiprin, cyclosporin A, tolmetin, apocynin, capsaicin, auranofin, indomethacin, gabapentin, glucametacin, gossypin, gossypetin, hibifolin, hypolaetin, cinmetacin, rapamycin, 15-deoxyspergualin, diacetyl-splenopentin, oroxindin, oxaprozin, oxamethacin, phenytoin, phenytoin-polyvinylpyrrolidone coprecipitate, phenytion in combination with phenobarbital, proglumetacin, tiopronin, trinitroglycerin, vigabatrin, butibufen, baclofen, benoxaprofen, carprofen, (S)(+) enantiomer of carprofen, fenoprofen, fenbufen, flunoxaprofen, flurbiprofen, ibuprofen, indoprofen, ketoprofen, loxoprofen, naproxen, pirprofen, suprofen, bucloxic acid, sulfanilamide ethylene polymer of 5-aminosalicylic acid, eicosapentaenoic acid, fenclozic acid, kojic acid, meclofenamic acid, metiazinic acid, mefenamic acid, flufenamic acid, 1-[(4-chlorophenyl)methyl]-2-methyl-5-(quinolinylmethoxy)-1H-indole-3-acetic acid, 1-isobutyl-3,4-diphenylpyrazole-5-acetic acid, 6-methoxy-2-naphthylacetic acid, (10-methoxy-4H-benzo[4,5]cyclohepta-[1,2-b]-thiophene-4-yliden)-acetic acid, niflumic acid, (Z)-3-[4-(acetyloxy)-5-ethyl-3-methoxy-1-naphthalenyl]-2-methyl-2-propenoic acid, tiaprofenic acid, 7-[3-(4-acetyl-3-methoxy-2-propylphenoxy)propoxy]-3,4-dihydro-8-propyl-2H-1-benzopyran-2-carboxylic acid, 4H-4-phenylthieno-[3,2-c]-[1]-benzopyran-2-carboxylic acid, salicylic acid, tolfenamic acid, valproic acid, benorylate, benztropine mesylate, clofibrate, diphenoxylate, diphenoxylate in combination with atropine sulfate, disodium azodisalicylate, felbamate, gold sodium thiomalate, methotrexate, isosorbide dinitrate, isosorbide 5-mononitrate, methotrexate sodium, D-myo-inositol-1.2.6-trisphosphate, meclofenamate, ethyl 2-amino-3-benzoylphenylacetate, imidazole 2-hydroxybenzoate, sodium 2-[4-(2-oxocyclopentylmethyl)phenyl]propionate dihydrate, tirilazad mesylate, piroxicam, clonazepam, diazepam, droxicam, isoxicam, lorazepam, meloxicam, sudoxicam, tenoxicam, nabumetone, emorfazone, glutathione, phenylbutazone, oxyphenbutazone, azapropazone, dapsone, primidone, paramethasone, paramethasone 21-acetate, paramethasone disodium phosphate, proquazone, feprazone, sulfinpyrazone, suxibuzone, phenidone, prenazone, primidone, 6-(2,4-difluorophenoxy)-5-methylsulfonyl-amino-1-indanone, 5-[[3,5-bis(1,1-dimethylethyl)-4-hydroxy-phenyl]methylene]-3-(dimethylamino)-4-thiazolidinone, 5-[[3,5-bis(1,1-dimethylethyl)-4-hydroxyphenyl]methylene]-3-(methylamino)-4-thiazolidinone, bumadizon-calcium, aurothioglucose, amiprilose, hydroxychloroquine, S-adenosylmethionine, amantadine, carbamazepine, S-carboxymethylcysteine, chloroquine, 4-(2-chlorophenyl)-2-[2-(4-isobutylphenyl)ethyl]-6,9-dimethyl-6H-thieno[3,2-f][1,2,4]triazolo[4,3a][1,4]diazepine, deferoxamine mesylate, diaveridine, dizocilpine, amodiaquine, quinacrine, azathioprine, 6-mercaptopurine, N-2-mercaptopropionylglycine, salicylsulfapyridine, diaveridine, lamotrigine, ethopropazine, olsalazine, oxametacine, 5-thiopyridoxine, ketorolac tromethamine, D-penicillamine, procyclidine, scopolamine, taurine, tinoridine, trimetazidine, sulfasalazine, acetazolamide, acetazolamide sodium, cyclophosphamide, 2,6-diamino-N-{[1-(1-oxotridecyl)-2-piperidinyl]-methyl}-hexanamide, 2-(2-hydroxy-4-methylphenyl)aminothiazole hydrochloride, hypolaetin-8-glucoside, quercetagetin-7-glucoside, diazo loperamide, ethosuximide, fluocinonide, flurandrenolide, leflunomide, difenpiramide, moclobemide, naphthypramide, nimesulide, sodium nitroprusside, zonisamide, lobenzarit, chlorambucil, solubilized chicken type II collagen, 1-p-chlorobenzyl-2-dimethyl-aminomethylcyclohexen-1,2, etoclofene, diflunisal, fendosal, perisoxal, phenobarbital, ditazol, acebutolol, alprenolol, allopurinol, atenolol, betaxolol, bethanechol, bimetopyrol, carbachol, carteolol, cirsiliol, esmolol, isoproterenol, labetalol, leucocyanidol, metoprolol, misoprostol, nadolol, oxprenolol, penbutolol, pindolol, propranolol, sotalol, timolol, tenidap, 4H-2-carboxamido-4-phenylthieno-[3,2-c]-[1]-benzopyran, divalproex sodium, dipyridamole, propentophylline, pentoxifylline, amitriptyline, diltiazem, verapamil, nifedipine, nicardipine, isradipine, amlodipine, felodipine, chlordiazepoxide, benazepril, captopril, enalapril, enalaprilat, fosinopril, lisinopril, ramipril, quinapril, quinapril in combination with hydrochlorothiazide, 4-aminopyridine, 3,4-diaminopyridine, milacemide, trihexyphenidyl, diphenhydramine, memantine, isoniazid, oxybutynin, oxybutynin chloride, propantheline, imipramine, phenoxybenzamine, tizanidine, chlorpromazine, diacetylrhein, alfa-2a interferon, alfa-2b interferon, alfa-N3 interferon, beta interferon, random polymer of [L-alanine, L-glutamic acid, L-lysine and L-tyrosine, ratio of 6.0:1.9:4.7:1.0] of molecular weight between 14,000 and 23,000 Daltons, cyclophosphamide, azathioprine, cyproheptadine, clemastine, setastine, nordihydroguaiaretic acid, ketoconazole, heparin, heparin calcium, heparin sodium, warfarin, ticlopidine, aminophylline, methohexital sodium, derivative of tirilazad in which the steroid portion of the chemical structure has been replaced with the tetramethyl chroman portion of d-α tocopherol, low molecular weight sulphate/dermatan sulphate glycoaminoglycan heparinoid mixtures of 6,500 Dalton mean molecular weight, lidocaine, procainamide, tilomisole, tepoxalin, scalaradial, indoxole, flumizole, bucolome, sideritoflavone, 1-[3-(naphth-2-ylmethoxy)phenyl]-1-(thiazol-2-yl)propyl methyl ether, epirizole, DL-2-(4-hexyloxyphenyl) glycine octyl ester, DL-2-[4-(5.5-dimethylhexyloxy)phenyl] glycine octyl ester, 2-(p-bromophenyl)-9-dimethylaminopropyl-9H-imidazo[1,2-α]-benzimidazole, glucosamine, N-acetylglucosamine, glucosamine sulfate salt and anakinra.

(xi) Administration of a Closed Group of Optional Pharmaceutically Acceptable Carriers Suitable for the Orally Administered Composition of the Present Invention It is further disclosed herein that the compositions and method of the present invention can include the incorporation of one or more optional pharmaceutically acceptable carrier suitable for the orally administered composition thereof selected from the closed group consisting of carboxymethyl cellulose, microcrystalline cellulose, cellulose, starch, dicalcium phosphate, tricalcium phosphate, stearic acid, magnesium stearate, silica, soy flour, watercress, yeast, alfalfa, parseley, lecithin, rice bran, gum tragacanth, gum guar, gum agar, gum arabic, gum carrageenan, gum ghatti, gum karaya, locust bean gum, gum mastic, gum mesquite and gum xanthan; wherein said optional pharmaceutically acceptable carrier is compounded together with at least one primary agent for systemic administration solely via the oral route in combination with at least one previously known medicament required co-agent for systemic administration solely via the oral route, and in combination with one or more additional required co-agent suitable for systemic administration solely via the oral route selected from the group consisting of antioxidants, vitamins, metabolites at risk of depletion, sulfhydryl co-agents, co-agents which may facilitate glutathione activity and nonabsorbable primary amine polymeric co-agents. Said incorporation of one or more optional pharmaceutically acceptable carrier suitable for the orally administered composition hereof may contribute to the overall utility of the composition. For example, said one or more optional pharmaceutically acceptable carrier suitable for the orally administered composition hereof may act as a factor in determining the rate at which the composition will dissolve subsequent to oral administration.

(xii) Factors Affecting Daily Dosage Schedule

A daily protocol of primary agent consumption, in combination with co-agents disclosed herein, may be defined such that the ingredients are administered in delayed-release, sustained-release and/or color coded tablets or capsules, so as to facilitate patient compliance and maximize therapeutic value. Said delayed-release tablets can consist, for example, of a composition of the present disclosure coated with Eudragit-S, an acrylic-based resin pH-dependent delayed release substance. Said sustained-release tablets can consist, for example, of a composition of the present disclosure coated with a semipermeable membrane of ethyl cellulose. Alternatively, a therapeutic composition may be incorporated into a foodstuff product, so as to encourage regular, long term patient compliance.

(xiii) Therapeutic Utilization

As indicated above the present invention is intended for the treatment of chronic inflammatory diseases and is useful for this purpose in various animal species, e. g., rodents, cats, dogs, cattle, sheep, horses, pigs, monkeys and other primates.

Two case histories regarding human subjects may serve to illustrate the practical application of the invention originally disclosed in U.S. patent application Ser. No. 07/906,909.

Case History One: Pearson and Shaw (1982, pg. 299) described the following summary of an arthritis patient taking vitamin E and vitamin A:

The correct dose of antioxidants for effective arthritis therapy must be determined by experimentation. The effective dose may be quite high. For example, a friend of ours who is a well-known artist in his fifties developed arthritis in his hands. This man's hands became so painful and stiff he could no longer use his fingers to remove the caps from his tubes of paint. He tried vitamin E at increasing dose levels. It was not until he got up to 10,000 I.U. of E and 20,000 I.U. of A per day that he obtained relief from the pain and crippling stiffness. His hands are now flexible and can be used to draw without difficulty. But they remain so only as long as our friend takes 10,000 I.U. of E and 20,000 I.U. of A a day, not less (he's tried).

This dosage of vitamin E far exceeds presently accepted levels of daily usage, which are generally regarded as being in the range of 400 I.U. per day. This particular combination of vitamins E and A, both lipophilic, would not be expected to inhibit any of the free radical reactions taking place in aqueous microenvironments. Nor would either of its two components chemically bind and thus deactivate any reactive aldehydes generated by lipid peroxidation associated with the inflammatory process that diffused out of a lipid microenvironment (such as a cell membrane) into an aqueous microenvironment (such as cell cytoplasm or the synovial fluid of a joint), such aldehydes being water soluble. Case History Two: Patient L.S. has a history of arthritis dating back to a serious automobile accident in 1980. By January of 1991 she had serious arthritic involvement of the lumbar spine and chronic hip and knee joint pain on a continuous basis. She had difficulty raising herself from a chair, required the assistance of a cane for activities as simple as walking from her front door to her car, was no longer able to go up or down a flight of stairs, and required use of a prescription analgesic drug every two hours during the night to sleep. She had participated in a program at the Pain Clinic of the University of Miami Medical School and at doctor's advice had used prescription drugs which included Clinoril (R) and Anaprox (R), both nonsteroidal anti-inflammatory agents. At the recommendation of this inventor, patient L.S. began orally consuming 800 I.U. vitamin E, 1. gm of L-methionine and 1.1 gm PABA per day for two months. Subsequently, vitamin E and L-methionine oral usage remained the same and PABA oral usage was increased to 2.2 gm per day, with the protocol continued on an indefinite basis.

When previously examined by an orthopedics physician a diagnosis was established which included:

... Lumbar spine X-Rays in AP and lateral views show extensive degenerative arthritic changes at multiple levels of the lumbar spine ... severe arthritic changes lumbar spine. Bursitis left greater trochanter clinically.... She will always have a problem related to her underlying degenerative disease involving her lower back.... She is favoring her left leg.... Her straight leg raising is limited on the left side....

Ten weeks after after initiating this inventor's orally consumed PABA/L-methionine/vitamin E protocol, patient L.S. reported that her arthritis-related pain was much decreased and her functional status much improved. By four months into use of this orally administered therapeutic protocol patient L.S. had stopped using her cane, had a walking gait which was much improved, had taken to raking leaves in the yard as a form of exercise, and no longer required nighttime prescription analgesics to sleep. At twelve months on this protocol, patient L. S. reported climbing and descending a flight of stairs without difficulty, and her ability to climb stairs has continued to improve. When re-examined by her orthopedic physician, who was not informed of her use of the PABA/L-methionine/vitamin E protocol, seven months after beginning therapy the doctor noted, in part:

This patient is markedly better. She has normal straight leg raising. She has no significant leg pain. She walks well on her toes and walks well on her heels now without any evidence of motor weakness. There is no limp present.

Unaware of the patient's collaborative effort with this inventor, the orthopedic physician was unable to provide an explanation of the marked improvement in the clinical status of patient L.S. At her office visit patient L. S. noted that she had stopped taking Anaprox, which her orthopedics physician had prescribed seven months earlier.

This inventor recognizes the novel, deliberate and original combination of primary amine benzoic acid derivatives as primary agents used with known antioxidant co-agents as a type of composition likely to have increased, possibly synergistic properties for the treatment of chronic inflammatory diseases. This inventive strategy for the clinical treatment of these diseases has not been previously recognized.

PABA, many of the other required primary amine primary agents, the required antioxidant co-agents, other required co-agents of the instant disclosure and required previously known medicament co-agents described herein are chemicals which have been previously synthesized and described.

Yet the new subject matter of the instant invention is the new and novel combination of these ingredients so as to obtain original compositions not anticipated by the prior art and a method of use therefor. The original invention, as defined in U.S. patent application Ser. No. 07/906,909, constitutes a significant and practical advancement of clinical therapeutic technology available for treating chronic inflammatory diseases, and the present invention constitutes a further practical non-obvious extension of the original inventive concept.

(xiv) Use of the Required Primary Agents Disclosed Above in Section (ii) and Required Use of the Co-Agents Disclosed Above in Sections (iv) through (ix) in Combination with at Least One Required Previously Known Medicament Co-Agent Disclosed Above in Section (x)

As summarized above, it is evident that presently available pharmaceutical technology for treatment of the diseases addressed herein is almost entirely symptomatic, as well as temporary and of partial clinical benefit, at best. The dosages of any of the previously known medicaments of Section (x) discussed herein, except those which are still the subjects of preliminary laboratory studies, are well known to those skilled in the art. Significant adverse side effects accompany many of these treatments, which limit their use. The present invention defines the use of previously recognized technology in combination with the invention originally described in U.S. patent application Ser. No. 07/906,909, so as to achieve greater clinical effectiveness in treatment of these diseases. In using the therapeutic technology defined herein, physicians may achieve in some cases the clinical benefits of one or more of the previously known medicaments of Section (x) while using lower dosage levels, thus minimizing adverse side effects. Within the context of the present invention, it is important to note the documentation provided by Flood and coworkers (1988). Their findings indicate that when drugs are used in combination they may provide beneficial effect at reduced dosages which are ineffective when drugs are administered alone. This approach may permit wider and more effective use of previously recognized drug technology for the substances included in the closed class of Section (x). It is acknowledged herein that for many of the previously known medicaments of Section (x) the optimum dosage must be determined on an individualized basis, and may be below or above the dosage range generally recognized for public use. It is to be understood that dosage ranges listed below refer to adult usage and that in particular cases it may be desirable to go beyond the dosage ranges noted below. The various ingredients of oral compositions noted below which exemplify the present invention may be formulated with additional components or coatings so as to function in a slow acting, delayed release manner. The previously known medicaments of Section (x) listed in the following examples are to be systemically administered via the oral route.

Example 1

Clinical treatment of chronic gingivitis and/or chronic periodontitis can be improved by use of a composition comprising at least one primary agent of Section (ii), and one or more required substance selected from those noted above in Section (iv) through Section (ix), and at least one required previously known medicament of Section (x) recognized as effective to treat chronic gingivitis and/or chronic periodontitis, such as, for example, (a) antibiotics such as penicillin G potassium (Pfizerpen, Roerig), dosage range from one million units daily to twenty million units daily;

penicillin G benzathine and penicillin G procaine combination (Bicillin C-R, Wyeth-Ayerst Laboratories), dosage range from 300,000 units to 2,400,000 units administered for one day or daily until subsidence of abnormally high body temperature;

penicillin V potassium (Veetids, Apothecon), dosage range from 500 mg daily to 2 gm daily;

erythromycin (E-Mycin, Boots Laboratories), dosage range from 250 mg daily to 5 gm daily;

amoxicillin (Amoxil, SmithKline Beecham), dosage range from 750 mg daily to 1.5 grams daily;

amoxicillin in combination with clavulanate potassium (Augmentin, SmithKline Beecham), dosage range from 750 mg amoxicillin and 187.5 mg clavulanate potassium daily to 1.5 grams amoxicillin and 375 mg clavulanate potassium daily;

tetracycline (Achromiycin V, Lederle), dosage range from 500 mg daily to 2 gm daily;

doxycycline (Vibramycin, Pfizer), dosage range from 50 mg daily to 300 mg daily; and minocycline (Minocin, Lederle), dosage range from 50 mg daily to 300 mg daily;

(b) nitroimidazoles such as metronidazole (Flagyl, Searle), dosage range from 250 mg daily to 2.5 gm daily;

(c) antiseptics such as chlorhexidine gluconate (Peridex oral rinse, Proctor & Gamble), one to three oral rinses per day;

(d) surfactants such as triclosan, as ingredient in mouthwash, dosage range of one to three applications of 0.01% to 5% solution or suspension daily; and sanguinarine, as ingredient in mouthwash, dosage range of one to three applications of 0.01% to 5% solution or suspension daily;

(e) ebselen, application of 1% to 25% compositions;

(f) nonsteroidal anti-inflammatory drugs administered orally including suprofen; dosage range from 5 mg/kg daily to 100 mg/kg daily; and (g) hydrocortisone acetate, dosage range from 1 mg daily to 400 mg daily.

The following illustrate specific formulations according to the present invention.

| | |
|---|---|
| p-aminobenzoic acid | 1 gm |
| d-α-tocopheryl succinate | 500 I.U. |
| penicillin G potassium | one million units |
| p-aminobenzoic acid, potassium salt | 20 gm |
| N-acetylcysteine | 10 gm |
| suprofen | 5 gm |
| p-aminomethylbenzoic acid | 5 gm |
| acetylhomocysteine thiolactone | 1 gm |
| metronidazole | 2 gm |

Example 2

Clinical treatment of chronic autoimmune gastritis can be improved by use of a composition comprising at least one primary agent of Section (ii), and one or more required substance selected from those noted above in Section (iv) through Section (ix), and at least one required previously known medicament of Section (x) recognized as effective to treat chronic autoimmune gastritis, such as, for example, (a) sodium guaiazulene-3-sulfonate, dosage range from 1 mg/kg daily to 20 mg/kg daily.

The following illustrate specific formulations according to the present invention.

| | |
|---|---|
| 4-amino-3-hydroxybenzoic acid | 1 gm |
| mixed tocopherols | 1,000 I.U. |
| sodium guaiazulene-3-sulfonate | 75 mg |
| p-aminobenzoic acid, potassium salt | 15 gm |
| L-Methionine | 1 gm |
| sodium guaiazulene-3-sulfonate | 1.5 gm |
| 5-amino-2-hydroxybenzoic acid | 5 gm |
| zinc carnosine | 70 mg |
| ebselen | 5 gm |
| sodium guaiazulene-3-sulfonate | 1.5 gm |

Example 3

Clinical treatment of ileitis, including Crohn's disease can be improved by use of a composition comprising at least one primary agent of Section (ii), and one or more required substance selected from those noted above in Section (iv) through Section (ix), and at least one required previously known medicament of Section (x) recognized as effective to treat ileitis, including Crohn's disease, such as, for example, (a) sulfasalazine (Azulfidine EN-tabs delayed release tablets and Azulfidine tablets, Kabi Pharmacia), dosage range from 1 gram daily to 5 grams daily;

(b) dexamethasone (Decadron, Merck & Co.), dosage range from 0.25 mg daily to 18 mg daily;

(c) methylprednisolone acetate (Depo-Medrol, Upjohn), dosage range from 0.5 mg daily to 50 mg daily, or weekly dosage of from 20 mg to 120 mg;

(d) hydrocortisone (Hydrocortone, Merck & Co.), dosage range from 1 mg daily to 400 mg daily;

(e) metronidazole (Flagyl, Searle), dosage range from 250 mg daily to 2.5 gm daily;

(f) prednisolone (Pediapred, Fisons), dosage range from 1 mg daily to 250 mg daily, or alternate day dosing;

(g) cortisone (Cortone, Merck & Co.), dosage range from 5 mg daily to 400 mg daily;

(h) prednisone (Deltasone, Upjohn), dosage range from 1 mg daily to 250 mg daily, or alternate day dosing;

(i) methylprednisolone (Medrol, Upjohn), dosage range from 1 mg daily to 250 mg daily, or alternate day dosing;

(j) triamcinolone (Aristocort, Fujisawa), dosage range from 1 mg daily to 200 mg daily, or alternate day dosing;

(k) triamcinolone diacetate, dosage range from 1 mg daily to 200 mg daily, or alternate day dosing;

(l) betamethasone (Celestone, Schering), dosage range from 0.2 mg daily to 12 mg daily, or alternate day dosing;

(m) betamethasone (Celestone Soluspan suspension, Schering), dosage range from 0.1 mg daily to 10 mg daily, or alternate day dosing; (n) dexamethasone (Decadron phosphate injection, Merck & Co.), dosage range from 0.1 mg daily to 10 mg daily;

(o) diphenoxylate, dosage range from 2.5 mg daily to 20 mg daily;

(p) diphenoxylate in combination with atropine sulfate (Lomotil, Searle), dosage range from 2.5 mg diphenoxylate and 25 μg atropine sulfate daily to 20 mg diphenoxylate and 200 μg atropine sulfate daily;

(q) deodorized opium tincture, dosage range from 0.5 ml daily to 3 ml daily;

(r) codeine, dosage range from 1 mg daily to 150 mg daily;

(s) azathioprine (Imuran, Burroughs Wellcome), dosage range from 0.1 mg/kg daily to 2.5 mg/kg daily;

(t) 6-mercaptopurine (Purinethol, Burroughs Wellcome), dosage range from 0.1 mg/kg daily to 2.5 mg/kg daily;

(u) cyclosporin A (Sandimmune, Sandoz Pharmaceutical), dosage range from 1 mg/kg daily to 15 mg/kg daily;

(v) methotrexate (Lederle), dosage range from 2.5 mg daily to 30 mg daily, or doses from 5 mg to 50 mg once or twice weekly; and (w) methotrexate sodium (Methotrexate LPF, Lederle), dosage range from 2.5 mg daily to 30 mg daily, or doses from 5 mg to 50 mg once or twice weekly.

The following illustrate specific formulations according to the present invention.

| | |
|---|---|
| trans-4-aminocyclohexane-carboxylic acid | 1 gm |
| α-tocopherol | 500 I.U. |
| prednisolone | 5 mg |
| p-aminobenzoic acid | 15 gm |
| zinc carnosine | 70 mg |
| diphenoxylate | 20 mg |
| 5-amino-2-methoxybenzoic acid | 5 gm |
| butylated-hydroxytoluene | 500 mg |
| dihydrolipoic acid | 250 mg |
| cyclosporin A | 100 mg |

Example 4

Clinical treatment of inflammatory bowel disease, including ulcerative colitis, can be improved by use of a composition comprising at least one primary agent of Section (ii), and one or more required substance selected from those noted above in Section (iv) through Section (ix), and at least one required previously known medicament of Section (x) recognized as effective to treat inflammatory bowel disease, including ulcerative colitis, such as, for example, (a) sulfasalazine (Azulfidine EN-tabs delayed release tablets and Azulfidine tablets, Kabi Pharmacia), dosage range from 1 gm daily to 5 gm daily;

(b) 7-[3-(4-acetyl-3-methoxy-2-propylphenoxy)propoxy]-3,4-dihydro-8-propyl-2H-1-benzopyran-2-carboxylic acid, dosage range from 0.1 mg/kg to 80 mg/kg;

(c) glutathione, dosage range from 1 mg/kg to 20 mg/kg;

(d) zileuton, dosage range from 100 mg daily to 1 gram daily;

(e) olsalazine (Dipentum, Pharmacia Ltd.), dosage range from 200 mg daily to 2 gm daily;

(f) disodium azodisalicylate, dosage range from 200 mg daily to 4 gm daily;

(g) dexamethasone (Decadron, Merck & Co.), dosage range from 0.1 mg daily to 18 mg daily;

(h) eicosapentaenoic acid (or commercial products containing this substance as the active ingredient, including Max-EPA capsules, 18 gm of which contains 3.2 gm eicosapentaenoic acid), dosage range from 500 mg daily to 10 gm daily;

(i) salicylsulfapyridine (Salazopyrin, Pharmacia AB), dosage range from 1 gm daily to 5 gm daily;

(j) diazo sulfanilamide ethylene polymer of 5-aminosalicylic acid, dosage range from 500 mg daily to 5 gm daily;

(k) hydrocortisone (Hydrocortone, Merck & Co.), dosage range from 1 mg daily to 400 mg daily;

(l) prednisolone (Pediapred, Fisons), dosage range from 1 mg daily or every other day to 250 mg daily;

(m) cortisone (Cortone, Merck & Co.), dosage range from 5 mg daily to 400 mg daily;

(n) prednisone (Deltasone, Upjohn), dosage range from 1 mg daily to 250 mg daily, or alternate day dosing;

(o) methylprednisolone (Medrol, Upjohn), dosage range from 1 mg daily to 250 mg daily, or alternate day dosing;

(p) methylprednisolone acetate (Depo-Medrol, Upjohn), dosage range from 0.5 mg daily to 50 mg daily, or weekly dosage of from 20 mg to 120 mg;

(q) triamcinolone (Aristocort, Fujisawa), dosage range from 1 mg daily to 200 mg daily, or alternate day dosing;

(r) triamcinolone diacetate, dosage range from 1 mg daily to 200 mg daily, or alternate day dosing;

(s) betamethasone (Celestone, Schering), dosage range from 0.2 mg daily to 12 mg daily, or alternate day dosing;

(t) betamethasone, dosage range from 0.1 mg daily to 10 mg daily, or alternate day dosing;

(u) azathioprine (Imuran, Burroughs Wellcome), dosage range from 0.1 mg/kg daily to 2.5 mg/kg daily;

(v) 6-mercaptopurine (Purinethol, Burroughs Wellcome), dosage range from 0.1 mg/kg daily to 2.5 mg/kg daily;

(w) diphenoxylate, dosage range from 2.5 mg daily to 20 mg daily;

(x) diphenoxylate in combination with atropine sulfate (Lomotil, Searle), dosage range from 2.5 mg diphenoxylate and 25 µg atropine sulfate daily to 20 mg diphenoxylate and 200 µg atropine sulfate daily;

(y) deodorized opium tincture, dosage range from 0.5 ml daily to 3 ml daily;

(z) codeine, dosage range from 1 mg daily to 150 mg daily;

(a') loperamide (Imodium, Janssen Pharmaceutica), dosage range from 2 mg daily to 16 mg daily;

(b') corticotropin (ACTH), dosage range from 25 units daily to 150 units daily;

(c') cyclosporin A (Sandimmune, Sandoz Pharmaceutical), dosage range from 1 mg/kg daily to 15 mg/kg daily;

(d') benztropine mesylate (Cogentin, Merck & Co.), dosage range from 0.5 mg daily to 10 mg daily;

(e') trihexyphenidyl (Artane, Lederle), dosage range from 2 mg daily to 20 mg daily;

(f') procyclidine (Kemadrin, Burroughs Wellcome), dosage range from 2 mg daily to 50 mg daily;

(g') biperiden (Akineton, Knoll Pharmaceuticals), dosage range from 0.5 mg daily to 10 mg daily;

(h') ethopropazine, dosage range from 10 mg daily to 500 mg daily;

(i') scopolamine, dosage range from 0.1 mg daily to 1 mg daily;

(j') benztropine mesylate, dosage range from 0.5 mg daily to 10 mg daily;

(k') biperiden lactate, dosage range from 0.5 mg daily to 10 mg daily;

(l') propantheline bromide (Pro-Banthine, Schiapparelli Searle), dosage range from 7.5 mg daily to 120 mg daily; and (m') oxybutynin chloride (Ditropan, Marion Merrell Dow), dosage range from 5 mg daily to 20 mg daily.

The following illustrate specific formulations according to the present invention.

| | |
|---|---|
| p-aminobenzoic acid | 1 gm |
| N-acetylcysteine | 1 gm |
| zileuton | 100 mg |
| p-aminobenzoic acid, potassium salt | 20 gm |

| | |
|---|---|
| d-α-tocopheryl succinate | 2,000 I.U. |
| dexamethasone (intramuscular dosage) | 10 mg |
| 4-guanidinobenzoic acid HCl | 5 gm |
| zinc carnosine | 70 mg |
| trihexyphenidyl | 10 mg |

Example 5

Clinical treatment of interstitial cystitis can be improved by use of a composition comprising at least one primary agent of Section (ii), and one or more required substance selected from those noted above in Section (iv) through Section (ix), and at least one required previously known medicament of Section (x) recognized as effective to treat interstitial cystitis, such as, for example, (a) propantheline bromide (Pro-Banthine, Schiapparelli Searle), dosage range from 7.5 mg daily to 120 mg daily;

(b) oxybutynin chloride (Ditropan, Marion Merrell Dow), dosage range from 5 mg daily to 20 mg daily;

(c) benztropine mesylate (Cogentin, Merck & Co.), dosage range from 0.5 mg daily to 10 mg daily;

(d) trihexyphenidyl (Artane, Lederle), dosage range from 2 mg daily to 20 mg daily;

(e) procyclidine (Kemadrin, Burroughs Wellcome), dosage range from 2 mg daily to 50 mg daily;

(f) biperiden (Akineton, Knoll Pharmaceuticals), dosage range from 0.5 mg daily to 10 mg daily;

(g) ethopropazine, dosage range from 10 mg daily to 500 mg daily;

(h) scopolamine, dosage range from 0.1 mg daily to 1 mg daily;

(i) benztropine mesylate, dosage range from 0.5 mg daily to 10 mg daily; and (j) biperiden lactate, dosage range from 0.5 mg daily to 10 mg daily.

The following illustrate specific formulations according to the present invention.

| | |
|---|---|
| p-aminobenzoic acid | 1 gm |
| d-α-tocopheryl succinate | 500 I.U. |
| benztropine mesylate | 1 mg |
| p-aminobenzoic acid, potassium salt | 20 gm |
| mixed tocopherols | 3,500 I.U. |
| N-acetylcysteine | 10 gm |
| oxybutynin chloride | 20 mg |
| o-aminomethylbenzoic acid | 5 gm |
| α-tocopherol nicotinate | 1,500 I.U. |
| dihydrolipoic acid | 250 mg |
| ethopropazine | 200 mg |

Example 6

Clinical treatment of psoriasis can be improved by use of a composition comprising at least one primary agent of Section (ii), and one or more required substance selected from those noted above in Section (iv) through Section (ix), and at least one required previously known medicament of Section (x) recognized as effective to treat psoriasis, such as, for example, (a) 7-[3-(4-acetyl-3-methoxy-2-propylphenoxy)propoxy]-3,4-di-hydro-8-propyl-2H-1-benzopyran-2-carboxylic acid, dosage range from 0.1 mg/kg daily to 80 mg/kg daily;

(b) eicosapentaenoic acid, dosage range from 1 gm daily to 5 gm daily;

(c) dexamethasone, dosage range from 0.1 mg daily to 18 mg daily;

(d) methotrexate (Rheumatrex, Lederle Laboratories), dosage range from 1 mg weekly to 20 mg weekly;

(e) hydrocortisone (Hydrocortone, Merck & Co.), dosage range from 1 mg daily to 400 mg daily;

(f) prednisolone (Pediapred, Fisons), dosage range from 1 mg daily or every other day to 250 mg daily;

(g) cortisone (Cortone, Merck & Co.), dosage range from 5 mg daily to 400 mg daily;

(h) prednisone (Deltasone, Upjohn), dosage range from 1 mg daily to 250 mg daily, or alternate day dosing;

(i) methylprednisolone (Medrol, Upjohn), dosage range from 1 mg daily to 250 mg daily, or alternate day dosing;

(j) methylprednisolone acetate, dosage range from 0.5 mg daily to 50 mg daily, or weekly dosage of from 20 mg to 120 mg;

(k) triamcinolone (Aristocort, Fujisawa), dosage range from 1 mg daily to 200 mg daily, or alternate day dosing;

(l) triamcinolone diacetate, dosage range from 1 mg daily to 200 mg daily, or alternate day dosing;

(m) betamethasone, dosage range from 0.1 mg daily to 12 mg daily, or alternate day dosing;

(n) hydrocortisone, dosage range from 1 mg daily to 400 mg daily;

(o) triamcinolone acetonide, dosage range from 1 mg daily to 100 mg daily;

(p) alclometasone 17,21-dipropionate, dosage range from 1 mg daily to 100 mg daily;

(q) fluticasone propionate, dosage range from 1 mg daily to 100 mg daily;

(r) betamethasone 17,21-dipropionate, dosage range from 1 mg daily to 100 mg daily;

(s) mometasone 17-(2-furoate) (Elocon, Schering), dosage range from 1 mg daily to 100 mg daily;

(t) clobetasol propionate (Temovate, Glaxo Dermatology), dosage range from 1 mg daily to 100 mg daily;

(u) methoxsalen, dosage range from 1 mg daily to 100 mg daily;

(v) methoxsalen (Oxsoralen-Ultra capsules, ICN), dosage range from one 10 mg capsule per month to two 10 mg capsules three times per week;

(w) etretinate (Tegison, Roche Dermatologics), dosage range from 0.125 mg/kg daily to 1.5 mg/kg daily;

(x) isotretinoin (Accutane, Roche Dermatologics), dosage range from 0.1 mg/kg daily to 2 mg/kg daily;

(y) anthralin, dosage range from 1 mg daily to 100 mg daily;

(z) cyclosporin A (Sandimmune, Sandoz Pharmaceutical), dosage range from 1 mg/kg daily to 15 mg/kg daily;

(a') vitamin $D_3$, dosage range from 0.1 mg/kg daily to 2 mg/kg daily; and (b') salicylic acid, dosage range from 0.1 mg/kg daily to 2 mg/kg daily.

The following illustrate specific formulations according to the present invention.

| | |
|---|---|
| 4-(aminoguanidino)benzoic acid | 1 gm |
| nordihydroguaiaretic acid | 7.5 gm |
| methylprednisolone | 2.5 mg |
| p-aminophenylacetic acid | 20 gm |
| probucol | 1 gm |
| etretinate | 100 mg |
| p-aminobenzoic acid | 5 gm |

-continued

| | |
|---|---|
| timonacic | 250 mg |
| cyclosporin A | 500 mg |

Example 7

Clinical treatment of rheumatoid arthritis can be improved by use of a composition comprising at least one primary agent of Section (ii), and one or more required substance selected from those noted above in Section (iv) through Section (ix), and at least one required previously known medicament of Section (x) recognized as effective to treat rheumatoid arthritis, such as, for example, (a) meclofenamate (Meclomen), dosage range from 100 mg daily to 800 mg daily;

(b) mefenamic acid (Ponstel), dosage range from 200 mg daily to 1.5 gm daily;

(c) flufenamic acid, dosage range from 100 mg daily to 1 gm daily;

(d) amfenac, dosage range from 1 µg/kg daily to 1 mg/kg daily;

(e) ethyl 2-amino-3-benzoylphenylacetate, dosage range from 10 µg/kg daily to 10 mg/kg daily;

(f) diclofenac (Voltaren), dosage range from 10 mg daily to 200 mg daily;

(g) etodolac (Lodine, Wyeth-Ayerst Laboratories), dosage range from 200 mg daily to 2 gm daily;

(h) metiazinic acid, dosage range from 1 mg/kg daily to 100 mg/kg daily; (i) indomethacin (Indocin), dosage range from 25 mg daily to 250 mg daily;

(j) fenclozic acid, dosage range from 2.5 mg/kg daily to 250 mg/kg daily;

(k) ketorolac tromethamine, dosage range from 5 mg daily to 150 mg daily;

(l) sulindac (Clinoril, Merck & Co.), dosage range from 50 mg daily to 500 mg daily;

(m) tolmetin (Tolectin), dosage range from 100 mg daily to 2 gm daily;

(n) glucametacin, dosage range from 50 mg daily to 600 mg daily;

(o) cinmetacin, dosage range from 2 mg/kg daily to 400 mg/kg daily;

(p) fenclofenac, dosage range from 200 mg daily to 2 gm daily;

(q) fenbufen, dosage range from 250 mg daily to 1.25 gm daily;

(r) butibufen, dosage range from 40 mg/kg daily to 400 mg/kg daily;

(s) ketorolac tromethamine (Toradol, Syntex), dosage range from 5 mg daily to 150 mg daily;

(t) tinoridine, dosage range from 2.5 mg/kg daily to 250 mg/kg daily;

(u) fenoprofen (Nalfon), dosage range from 250 mg daily to 3.2 gm daily;

(v) flurbiprofen (Ansaid), dosage range from 50 mg daily to 500 mg daily;

(w) ibuprofen (Motrin), dosage range from 200 mg daily to 3.2 gm daily;

(x) ketoprofen (Orudis), dosage range from 25 mg daily to 500 mg daily;

(y) naproxen (Naprosyn), dosage range from 125 mg daily to 1.25 gm daily;

(z) bucloxic acid, dosage range from 200 mg daily to 2 gm daily;

(a') the (S)(+) enantiomer of carprofen, dosage range from 10 mg daily to 750 mg daily;

(b') phenylbutazone (Azolid), dosage range from 2 mg/kg daily to 100 mg/kg daily;

(c') oxyphenbutazone (Taneril), dosage range from 100 mg daily to 1 gm daily;

(d') feprazone, dosage range from 100 mg daily to 1.5 gm daily;

(e') carprofen, dosage range from 0.2 mg/kg daily to 50 mg/kg daily;

(f') diflunisal, dosage range from 250 mg daily to 1.5 gm daily;

(g') sulfasalazine, dosage range from 200 mg daily to 3 gm daily;

(h') benorylate, dosage range from 1 gm daily to 7 gm daily;

(i') piroxicam (Feldene), dosage range from 5 mg daily to 25 mg daily;

(j') isoxicam, dosage range from 50 mg daily to 500 mg daily;

(k') auranofin (Ridaura, SmithKline Beecham), dosage range from 1 mg daily to 9 mg daily;

(l') aurothioglucose, dosage range from 1 mg weekly to 40 mg weekly;

(m') gold sodium thiomalate, dosage range from 1 mg weekly to 50 mg weekly;

(n') hydroxychloroquine (Plaquenil, Sanofi Winthrop Pharmaceuticals), dosage range from 50 mg (equivalent to 39 mg base) daily to 600 mg (equivalent to 465 mg base) daily;

(o') chloroquine, dosage range from 50 mg daily to 500 mg daily;

(p') methotrexate (Rheumatrex, Lederle Laboratories), dosage range from 1 mg weekly to 20 mg weekly;

(q') D-penicillamine (Cuprimine, Merck & Co.), dosage range from 25 mg daily to 1.5 grams daily;

(r') cyclophosphamide (Cytoxan, Bristol-Myers Oncology), dosage range from 0.1 mg/kg daily to 5 mg/kg daily;

(s') prednisone (Deltasone, Upjohn), dosage range from 1 mg daily to 250 mg daily, or alternate day dosing;

(t') dexamethasone (Decadron, Merck & Co.), dosage range from 0.25 mg daily to 18 mg daily;

(u') methylprednisolone (Medrol, Upjohn), dosage range from 1 mg daily to 250 mg daily, or alternate day dosing;

(v') (10-methoxy-4H-benzo[4,5]cyclohepta-[1,2-b]-thiophene-4-yliden)-acetic acid, dosage range from 0.5 mg/kg daily to 100 mg/kg daily;

(w') cyclosporin A (Sandimmune, Sandoz Pharmaceutical), dosage range from 1 mg/kg daily to 250 mg/kg daily or three times weekly;

(x') rapamycin, dosage range from 1 mg/kg daily to 250 mg/kg daily or three times weekly;

(y') azathioprine, dosage range from 75 µg/kg daily to 2.5 mg/kg daily;

(z') nabumetone (Relafen, SmithKline Beecham), dosage range from 200 mg daily to 2 gm daily;

(a") eicosapentaenoic acid, dosage range from 500 mg daily to 10 gm daily;

(b") aloxiprin, dosage range from 1 gm daily to 7 gm daily;

(c") azapropazone, dosage range from 100 mg daily to 5 gm daily;

(d") amiprilose, dosage range from 1 gm daily to 8 gm daily;

(e''') chlorambucil (Leukeran, Burroughs Wellcome), dosage range from 0.5 mg daily to 10 mg daily;

(f") aceclofenac, dosage range from 0.2 mg/kg daily to 10 mg/kg daily;

(g") apocynin, dosage range from 1 mg/kg daily to 100 mg/kg daily;

(h") capsaicin, dosage range from 5 mg/kg daily to 200 mg/kg daily;

(i") 6-(2,4-difluorophenoxy)-5-methylsulfonylamino-1-indanone (Ciba-Geigy AG), dosage range from 0.2 mg/kg daily to 20 mg/kg daily;

(j") dapsone, dosage range from 20 mg daily to 200 mg daily;

(k") solubilized chicken type II collagen, dosage range from 50 µg daily to 20 mg daily;

(l") 15-deoxyspergualin, dosage range from 0.5 mg/kg daily to 10 mg/kg daily;

(m") diacetyl-splenopentin, dosage range from 100 µg/kg daily to 3 mg/kg daily;

(n") diaveridine, dosage range from 25 mg/kg daily to 500 mg/kg daily;

(o") ditazol, dosage range from 25 mg/kg daily to 750 mg daily;

(p") droxicam, dosage range from 0.1 mg/kg daily to 50 mg/kg daily;

(q") (Z)-3-[4-(acetyloxy)-5-ethyl-3-methoxy-1-naphthalenyl]-2-methyl-2-propenoic acid, dosage range from 10 mg/kg daily to 500 mg/kg daily;

(r") 1-p-chlorobenzyl-2-dimethyl-amino-methylcyclohexen-1,2, dosage range from 2.5 mg/kg daily to 250 mg/kg daily;

(s") etoclofene, intravenous, intramuscular, subcutaneous or oral dosage range from 1 mg/kg daily to 400 mg/kg daily;

(t") felbinac, dosage range from 100 mg daily to 1.25 gm daily;

(u") fenclorac, dosage range from 0.5 mg/kg daily to 50 mg/kg daily;

(v") fendosal, dosage range from 5 mg/kg daily to 200 mg/kg daily;

(w") isoxepac, dosage range from 200 mg daily to 2 gm daily;

(x") leflunomide, dosage range from 50 µg daily to 50 mg daily;

(y") lobenzarit, dosage range from 50 mg daily to 750 mg daily;

(z") lonazolac-Ca, dosage range from 100 mg daily to 1 gm daily;

(a''') 5-[[3,5-bis(1,1-dimethylethyl)-4-hydroxyphenyl]methylene]-3-(dimethylamino)-4-thiazolidinone, dosage range from 1 mg/kg daily to 100 mg/kg daily;

(b''') 5-[[3,5-bis(1,1-dimethylethyl)-4-hydroxyphenyl]methylene]-3-(methylamino)-4-thiazolidinone, dosage range from 1 mg/kg daily to 100 mg/kg daily;

(c''') bumadizon-calcium (Eumotol), dosage range from 100 mg daily to 1 gm daily;

(d''') azapropazone, dosage range from 100 mg daily to 1 gm daily;

(e''') D-myo-inositol-1.2.6-trisphosphate, dosage range from 10 mg/kg daily to 1.5 gm daily;

(f''') tenidap (Pfizer), dosage range from 25 mg daily to 2 gm daily;

(g''') ibufenac, dosage range from 1 mg/kg daily to 100 mg/kg daily;

(h''') nimesulide, dosage range from 100 mg daily to 2 gm daily;

(i''') oxametacine, dosage range from 50 mg daily to 500 mg daily;

(j''') oxaprozin, dosage range from 150 mg daily to 1.5 gm daily;

(k''') suxibuzone, dosage range from 2 mg/kg daily to 150 mg/kg daily;

(l''') pirprofen, dosage range from 100 mg daily to 1.5 gm daily;

(m''') proquazone, dosage range from 150 mg daily to 1.5 gm daily;

(n''') triamcinolone acetonide, dosage range from 5 µg/kg daily to 0.1 mg/kg daily;

(o''') suprofen; dosage range from 5 mg/kg daily to 100 mg/kg daily;

(p''') tenoxicam, dosage range from 5 mg daily to 40 mg daily;

(q''') tiaprofenic acid, dosage range from 100 mg daily to 1 gm daily;

(r''') tolfenamic acid, dosage range from 100 mg daily to 600 mg daily;

(s''') difenpiramide, dosage range from 250 mg daily to 1.5 gm daily;

(t''') isofezolac, dosage range from 0.5 mg/kg daily to 50 mg/kg daily;

(u''') tiopronin, dosage range from 5 mg/kg daily to 100 mg/kg daily;

(v''') 5-thiopyridoxine, dosage range from 50 mg daily to 2 gm daily;

(w''') hydrocortisone (Hydrocortone, Merck & Co.), dosage range from 1 mg daily to 400 mg daily;

(x''') prednisolone (Pediapred, Fisons), dosage range from 1 mg daily or every other day to 250 mg daily;

(y''') cortisone (Cortone, Merck & Co.), dosage range from 5 mg daily to 400 mg daily;

(z''') methylprednisolone acetate, dosage range from 0.5 mg daily to 50 mg daily, or weekly dosage of from 20 mg to 120 mg;

(a'''') triamcinolone (Aristocort, Fujisawa), dosage range from 1 mg daily to 200 mg daily, or alternate day dosing;

(b'''') triamcinolone diacetate, dosage range from 1 mg daily to 200 mg daily, or alternate day dosing;

(c'''') betamethasone, dosage range from 0.1 mg daily to 12 mg daily, or alternate day dosing;

(d'''') dexamethasone, dosage range from 0.1 mg daily to 10 mg daily;

(e'''') sulfasalazine (Azulfidine EN-tabs delayed release tablets and Azulfidine tablets, Kabi Pharmacia), dosage range from 1 gm daily to 5 gm daily;

(f'''') cyclophosphamide, dosage range from 0.1 mg/kg daily to 5 mg/kg daily, 2 mg/kg to 5 mg/kg twice weekly or 10 mg/kg to 15 mg/kg every seven to ten days;

(g'''') N,N'-diphenyl-p-phenylenediamine, dosage range from 10 mg/kg daily to 250 mg/kg daily;

(h'''') glucosamine, dosage range from 100 mg daily to 10 gm daily;

(i'''') N-acetylglucosamine, dosage range from 100 mg daily to 10 gm daily;

(j'''') glucosamine sulfate salt (Dona), dosage range from 100 mg daily to 10 gm daily; and (k'''') anakinra, dosage range from 20 mg daily to 300 mg daily.

The following illustrate specific formulations according to the present invention.

| | |
|---|---|
| 4-guanidinobenzoic acid HCl | 1 gm |
| mixed tocopherols | 500 I.U. |
| prednisone | 5 mg |
| p-aminobenzoic acid | 20 gm |
| d-α-tocopheryl succinate | 3,500 I.U. |
| L-methionine | 2 gm |
| sulindac | 500 mg |

-continued

| | |
|---|---|
| 4-(aminoguanidino)benzoic acid | 5 gm |
| acetylhomocysteine thiolactone | 1 gm |
| azathioprine | 75 mg |

Example 8

Clinical treatment of ankylosing spondylitis can be improved by use of a composition comprising at least one primary agent of Section (ii), and one or more required substance selected from those noted above in Section (iv) through Section (ix), and at least one required previously known medicament of Section (x) recognized as effective to treat ankylosing spondylitis, such as, for example, (a) isoxicam, dosage range from 25 mg daily to 400 mg daily;
(b) ketoprofen, dosage range from 50 mg daily to 500 mg daily;
(c) diclofenac, dosage range from 25 mg daily to 500 mg daily;
(d) fenclofenac, dosage range from 150 mg daily to 1.5 gm daily;
(e) phenylbutazone, dosage range from 50 mg daily to 400 mg daily;
(f) prenazone, dosage range from 1 mg/kg daily to 100 mg/kg daily;
(g) nabumetone, dosage range from 200 mg daily to 2 gm daily;
(h) indomethacin, dosage range from 50 mg daily to 500 mg daily;
(i) sulindac (Clinoril, Merck & Co.), dosage range from 50 mg daily to 500 mg daily;
(j) carprofen, dosage range from 25 mg daily to 300 mg daily;
(k) dexamethasone, dosage range from 0.1 mg daily to 18 mg daily;
(l) proquazone, dosage range from 150 mg daily to 1.5 gm daily;
(m) ibuprofen, dosage range from 200 mg daily to 2 gm daily;
(n) tenoxicam, dosage range from 5 mg daily to 50 mg daily;
(o) piroxicam, dosage range from 5 mg daily to 50 mg daily;
(p) tiaprofenic acid, dosage range from 100 mg daily to 1 gm daily;
(q) tolfenamic acid, dosage range from 100 mg daily to 1 gm daily;
(r) pirprofen, dosage range from 150 mg daily to 1.5 gm daily;
(s) hydrocortisone (Hydrocortone, Merck & Co.), dosage range from 1 mg daily to 400 mg daily;
(t) prednisolone (Pediapred, Fisons), dosage range from 1 mg daily or every other day to 250 mg daily;
(u) cortisone (Cortone, Merck & Co.), dosage range from 5 mg daily to 400 mg daily;
(v) prednisone (Deltasone, Upjohn), dosage range from 1 mg daily to 250 mg daily, or alternate day dosing;
(w) methylprednisolone (Medrol, Upjohn), dosage range from 1 mg daily to 250 mg daily, or alternate day dosing;
(x) methylprednisolone acetate, dosage range from 0.5 mg daily to 50 mg daily, or weekly dosage of from 20 mg to 120 mg;
(y) triamcinolone (Aristocort, Fujisawa), dosage range from 1 mg daily to 200 mg daily, or alternate day dosing;
(z) triamcinolone diacetate, dosage range from 1 mg daily to 200 mg daily, or alternate day dosing;
(a') betamethasone, dosage range from 0.1 mg daily to 12 mg daily, or alternate day dosing;
(b') imidazole 2-hydroxybenzoate, dosage range from 50 μmol/kg daily to 0.5 mmol/kg daily;
(c') diflunisal, dosage range from 250 mg daily to 1.5 gm daily;
(d') sulfasalazine, dosage range from 200 mg daily to 3 gm daily;
(e') benorylate, dosage range from 1 gm daily to 7 gm daily;
(f') naproxen (Naprosyn), dosage range from 125 mg daily to 1.25 gm daily;
(g') oxyphenbutazone (Taneril), dosage range from 100 mg daily to 1 gm daily;
(h') glucosamine, dosage range from 100 mg daily to 10 gm daily;
(i') N-acetylglucosamine, dosage range from 100 mg daily to 10 gm daily; and
(j') glucosamine sulfate salt (Dona), dosage range from 100 mg daily to 10 gm daily.

The following illustrate specific formulations according to the present invention.

| | |
|---|---|
| 4-aminophenylacetic acid | 1 gm |
| propyl gallate | 100 mg |
| indomethacin | 50 mg |
| 4-(guanidino)-2-methoxybenzoic acid | 15 gm |
| tert-butylhydroquinone | 1 gm |
| glycine | 10 gm |
| cortisone | 400 mg |
| 4-(aminoguanidino)benzoic acid | 5 gm |
| homocysteine | 1 gm |
| naproxen | 500 mg |

Example 9

Clinical treatment of osteoarthritis can be improved by use of a composition comprising at least one primary agent of Section (ii), and one or more required substance selected from those noted above in Section (iv) through Section (ix), and at least one required previously known medicament of Section (x) recognized as effective to treat osteoarthritis, such as, for example, (a) prednisone (Deltasone, Upjohn), dosage range from 1 mg daily to 250 mg daily, or alternate day dosing;
(b) nabumetone (Relafen, SmithKline Beecham), dosage range from 200 mg daily to 2 grams daily;
(c) ketoprofen (Orudis), dosage range from 25 mg daily to 500 mg daily;
(d) phenylbutazone, dosage range from 100 mg daily to 500 mg daily;
(e) the (S)(+) enantiomer of carprofen, dosage range from 50 mg daily to 750 mg daily;
(f) dexamethasone, dosage range from 0.1 mg daily to 18 mg daily;
(g) diclofenac (Voltaren), dosage range from 10 mg daily to 200 mg daily;
(h) diflunisal, dosage range from 250 mg daily to 1.5 gm daily;
(i) diphenpyramide, dosage range from 250 mg daily to 1.5 gm daily;
(j) fenbufen, dosage range from 250 mg daily to 1.25 gm daily;

(k) oxyphenbutazone (Taneril), dosage range from 100 mg daily to 1 gm daily;

(l) indomethacin (Indocin), dosage range from 25 mg daily to 250 mg daily;

(m) glucametacin, dosage range from 50 mg daily to 600 mg daily;

(n) isoxicam, dosage range from 50 mg daily to 500 mg daily;

(o) lonazolac-Ca, dosage range from 100 mg daily to 1 gm daily;

(p) S-adenosylmethionine, dosage range from 500 mg daily to 10 gm daily;

(q) bumadizon-calcium (Eumotol), dosage range from 100 mg daily to 1 gm daily;

(r) diacetylrhein, dosage range from 10 mg daily to 500 mg daily;

(s) proquazone, dosage range from 150 mg daily to 1.5 gm daily;

(t) naproxen (Naprosyn), dosage range from 0.5 mg/kg daily to 25 mg/kg daily;

(u) nimesulide, dosage range from 100 mg daily to 2 gm daily;

(v) oxametacine, dosage range from 50 mg daily to 500 mg daily;

(w) pirprofen, dosage range from 100 mg daily to 1.5 gm daily;

(x) prenazone, dosage range from 150 mg daily to 1.5 gm daily;

(y) sulindac (Clinoril, Merck & Co.), dosage range from 50 mg daily to 500 mg daily;

(z) suprofen, dosage range from 5 mg/kg daily to 100 mg/kg daily;

(a') tenoxicam, dosage range from 5 mg daily to 40 mg daily;

(b') tiaprofenic acid, dosage range from 100 mg daily to 1 gm daily;

(c') hydrocortisone (Hydrocortone, Merck & Co.), dosage range from 1 mg daily to 400 mg daily;

(d') prednisolone (Pediapred, Fisons), dosage range from 1 mg daily or every other day to 250 mg daily;

(e') cortisone (Cortone, Merck & Co.), dosage range from 5 mg daily to 400 mg daily;

(f') methylprednisolone (Medrol, Upjohn), dosage range from 1 mg daily to 250 mg daily, or alternate day dosing;

(g') methylprednisolone acetate, dosage range from 0.5 mg daily to 50 mg daily, or weekly dosage of from 20 mg to 120 mg;

(h') triamcinolone (Aristocort, Fujisawa), dosage range from 1 mg daily to 200 mg daily, or alternate day dosing;

(i') triamcinolone diacetate, dosage range from 1 mg daily to 200 mg daily, or alternate day dosing;

(j') betamethasone, dosage range from 0.1 mg daily to 12 mg daily, or alternate day dosing;

(k') etodolac (Lodine, Wyeth-Ayerst Laboratories), dosage range from 200 mg daily to 2 gm daily;

(l') glucosamine, dosage range from 100 mg daily to 10 gm daily;

(m') N-acetylglucosamine, dosage range from 100 mg daily to 10 gm daily; and (n') glucosamine sulfate salt (Dona), dosage range from 100 mg daily to 10 gm daily.

The following illustrate specific formulations according to the present invention.

| | |
|---|---|
| 4-amino-2-methylbenzoic acid | 1 gm |
| N,N'-dimethylthiourea | 300 mg |
| etodolac | 200 mg |
| p-aminobenzoic acid | 15 gm |
| β-carotene | 300 mg |
| dexamethasone | 10 mg |
| (4-aminocyclohexane)acetic acid | 5 gm |
| D-myo-inositol-1.2.6-trisphosphate | 20 gm |
| suprofen | 3 gm |

Example 10

Clinical treatment of tendinitis or tenosynovitis can be improved by use of a composition comprising at least one primary agent of Section (ii), and one or more required substance selected from those noted above in Section (iv) through Section (ix), and at least one required previously known medicament of Section (x) recognized as effective to treat tendinitis or tenosynovitis, such as, for example, (a) the (S)(+) enantiomer of carprofen, dosage range from 50 mg daily to 750 mg daily;

(b) dexamethasone, dosage range from 0.1 mg daily to 18 mg daily;

(c) diclofenac (Voltaren), dosage range from 10 mg daily to 200 mg daily;

(d) fenbufen, dosage range from 250 mg daily to 1.25 gm daily;

(e) nimesulide, dosage range from 100 mg daily to 2 gm daily;

(f) oxamethacin, dosage range from 50 mg daily to 500 mg daily;

(g) pirprofen, dosage range from 100 mg daily to 1.5 gm daily;

(h) proquazone, dosage range from 150 mg daily to 1.5 gm daily;

(i) sulindac (Clinoril, Merck & Co.), dosage range from 50 mg daily to 500 mg daily;

(j) tenoxicam, dosage range from 5 mg daily to 40 mg daily;

(k) tiaprofenic acid, dosage range from 100 mg daily to 1 gm daily.

(l) hydrocortisone (Hydrocortone, Merck & Co.), dosage range from 1 mg daily to 400 mg daily;

(m) prednisolone (Pediapred, Fisons), dosage range from 1 mg daily or every other day to 250 mg daily;

(n) cortisone (Cortone, Merck & Co.), dosage range from 5 mg daily to 400 mg daily;

(o) prednisone (Deltasone, Upjohn), dosage range from 1 mg daily to 250 mg daily, or alternate day dosing;

(p) methylprednisolone (Medrol, Upjohn), dosage range from 1 mg daily to 250 mg daily, or alternate day dosing;

(q) methylprednisolone acetate, dosage range from 0.5 mg daily to 50 mg daily, or weekly dosage of from 20 mg to 120 mg;

(r) triamcinolone (Aristocort, Fujisawa), dosage range from 1 mg daily to 200 mg daily, or alternate day dosing;

(s) triamcinolone diacetate, dosage range from 1 mg daily to 200 mg daily, or alternate day dosing;

(t) betamethasone, dosage range from 0.1 mg daily to 12 mg daily, or alternate day dosing;

(u) dexamethasone acetate, dosage range from 0.1 mg daily to 10 mg daily; and (v) indomethacin (Indocin), dosage range from 25 mg daily to 250 mg daily.

The following illustrate specific formulations according to the present invention.

| | |
|---|---|
| 4-amino-2-hydroxycyclohexanecarboxylic acid | 1 gm |
| 2-aminomethyl-4-tert-butyl-6-propionylphenol | 1.5 gm |
| indomethacin | 200 mg |
| p-aminobenzoic acid, potassium salt | 20 gm |
| ebselen | 20 gm |
| carprofen | 1 gm |
| 3,5-diaminobenzoic acid | 5 gm |
| butylated hydroxyanisole | 20 gm |
| dexamethasone acetate | 5 mg |

Example 11

Clinical treatment of carpel tunnel syndrome and other cumulative trauma disorders can be improved by use of a composition comprising at least one primary agent of Section (ii), and one or more required substance selected from those noted above in Section (iv) through Section (ix), and at least one required previously known medicament of Section (x) recognized as effective to treat carpel tunnel syndrome and other cumulative trauma disorders, such as, for example, (a) diclofenac (Voltaren), dosage range from 10 mg daily to 200 mg daily;

(b) dexamethasone acetate, dosage range from 0.1 mg daily to 10 mg daily;

(c) hydrocortisone acetate, dosage range from 1 mg daily to 400 mg daily; and (d) methylprednisolone acetate, dosage range from 0.5 mg daily to 50 mg daily, or weekly dosage of from 20 mg to 120 mg.

The following illustrate specific formulations according to the present invention.

| | |
|---|---|
| 4-amino-2-(methoxy)cyclohexanecarboxylic acid | 1 gm |
| 2-(2-hydroxy-4-methylphenyl)aminothiazole hydrochloride | 100 mg |
| dexamethasone acetate | 10 mg |
| p-aminophenylacetic acid, potassium salt | 20 gm |
| d-α-tocopheryl succinate | 3,000 I.U. |
| diclofenac | 200 mg |
| 4-amino-2-methylbenzoic acid, potassium salt | 5 gm |
| N,N'-diphenyl-p-phenylenediamine | 10 gm |
| hydrocortisone acetate | 100 mg |

Example 12

Clinical treatment of chronic discoid or systemic lupus erythematosus can be improved by use of a composition comprising at least one primary agent of Section (ii), and one or more required substance selected from those noted above in Section (iv) through Section (ix), and at least one required previously known medicament of Section (x) recognized as effective to treat chronic discoid or systemic lupus erythematosus, such as, for example, (a) hydroxychloroquine (Plaquenil, Sanofi Winthrop Pharmaceuticals), dosage range from 50 mg (equivalent to 39 mg base) daily to 400 mg (equivalent to 310 mg base) daily;

(b) quinacrine, dosage range from 10 mg daily to 200 mg daily;

(c) chloroquine, dosage range from 50 mg daily to 750 mg daily;

(d) amodiaquine, dosage range from 10 mg daily to 500 mg daily;

(e) triquine composition tablets (each tablet consisting of 25 mg quinacrine, 65 mg chloroquine and 50 mg hydroxychloroquine), dosage range from one quarter tablet daily to two tablets daily;

(f) 15-deoxyspergualin, dosage range from 0.5 mg/kg daily to 10 mg/kg daily;

(g) dexamethasone, dosage range from 0.1 mg daily to 18 mg daily;

(h) leflunomide, dosage range from 50 μg daily to 50 mg daily;

(i) cyclosporin A, dosage range from 0.1 mg daily to 100 mg daily;

(j) methylprednisolone (Medrol, Upjohn), dosage range from 1 mg daily to 250 mg daily, or alternate day dosing;

(k) eicosapentaenoic acid (or commercial products containing this substance as the active ingredient, including Max-EPA capsules, 18 gm of which contains 3.2 gm eicosapentaenoic acid), dosage range from 500 mg daily to 10 gm daily.

(l) hydrocortisone (Hydrocortone, Merck & Co.), dosage range from 1 mg daily to 400 mg daily;

(m) prednisolone (Pediapred, Fisons), dosage range from 1 mg daily or every other day to 250 mg daily;

(n) cortisone (Cortone, Merck & Co.), dosage range from 5 mg daily to 400 mg daily;

(o) prednisone (Deltasone, Upjohn), dosage range from 1 mg daily to 250 mg daily, or alternate day dosing;

(p) methylprednisolone acetate, dosage range from 0.5 mg daily to 50 mg daily, or weekly dosage of from 20 mg to 120 mg;

(q) triamcinolone (Aristocort, Fujisawa), dosage range from 1 mg daily to 200 mg daily, or alternate day dosing;

(r) triamcinolone diacetate, dosage range from 1 mg daily to 200 mg daily, or alternate day dosing;

(s) hydrocortisone acetate, dosage range from 1 mg daily to 400 mg daily;

(t) triamcinolone acetonide, dosage range from 1 mg daily to 100 mg daily;

(u) fluocinolone acetonide, dosage range from 1 mg daily to 100 mg daily;

(v) fluocinonide, dosage range from 1 mg daily to 100 mg daily;

(w) flurandrenolide, dosage range from 1 mg daily to 100 mg daily;

(x) betamethasone valerate, dosage range from 1 mg daily to 100 mg daily;

(y) betamethasone 17,21-dipropionate, dosage range from 1 mg daily to 100 mg daily;

(z) azathioprine (Imuran, Burroughs Wellcome), dosage range from 0.1 mg/kg daily to 2.5 mg/kg daily; and (a') cyclophosphamide, dosage range from 0.1 mg/kg daily to 5 mg/kg daily.

The following illustrate specific formulations according to the present invention.

| | |
|---|---|
| 3,5-diaminobenzoic acid | 1 gm |
| (+)-α-tocopherol acetate | 500 I.U. |
| hydroxychloroquine | 50 mg |
| p-aminophenylacetic acid | 20 gm |
| mixed tocopherols | 3,500 I.U. |
| 15-deoxyspergualin | 500 mg |
| 4-guanidinobenzoic acid, potassium salt | 5 gm |
| coenzyme Q | 200 mg |
| cyclophosphamide | 150 mg |

Example 13

Clinical treatment of pneumoconiosis due to inhalation of asbestos particles (asbestosis), inhalation of stone dust or quartz (silicosis) or inhalation of other causitive agents such as graphite, coal dust, particles produced by metal grinding, talc or corn dust can be improved by use of a composition comprising at least one primary agent of Section (ii), and one or more required substance selected from those noted above in Section (iv) through Section (ix), and at least one required previously known medicament of Section (x) recognized as effective to treat pneumoconiosis due to inhalation of asbestos particles (asbestosis), inhalation of stone dust or quartz (silicosis) or inhalation of other causitive agents such as graphite, coal dust, particles produced by metal grinding, talc or corn dust, such as, for example, (a) D-penicillamine (Cuprimine, Merck & Co.), dosage range from 25 mg daily to 1.5 gm daily;
(b) 4H-4-phenylthieno-[3,2-c]-[1]-benzopyran-2-carboxylic acid, dosage range from 0.5 mg/kg daily to 50 mg/kg daily;
(c) 4H-2-carboxamido-4-phenylthieno-[3,2-c]-[1]-benzopyran, dosage range from 0.5 mg/kg daily to 50 mg/kg daily;
(d) dexamethasone (Decadron, Merck & Co.), dosage range from 0.1 mg daily to 18 mg daily;
(e) indomethacin (Indocin), dosage range from 25 mg daily to 250 mg daily;
(f) prednisolone (Pediapred, Fisons), dosage range from 1 mg daily or every other day to 250 mg daily;
(g) hydrocortisone, dosage range from 1 mg daily to 400 mg daily;
(h) flurbiprofen (Ansaid), dosage range from 50 mg daily to 500 mg daily; and
(i) S-carboxymethylcysteine, dosage range from 1 mg/kg daily to 100 mg/kg daily.

The following illustrate specific formulations according to the present invention.

| | |
|---|---|
| 3,5-diaminophenylacetic acid | 1 gm |
| butylated hydroxyanisole | 10 mg |
| N-acetylcysteine | 500 mg |
| p-aminobenzoic acid | 20 gm |
| 2-aminomethyl-4-tert-butyl-6-propionylphenol | 20 gm |
| prednisolone | 100 mg |
| 4-amino-2-methoxycyclohexanecarboxylic acid | 5 gm |
| tert-butylhydroquinone | 500 mg |
| D-penicillamine | 100 mg |

Example 14

Clinical treatment of chronic obstructive pulmonary disease can be improved by use of a composition comprising at least one primary agent of Section (ii), and one or more required substance selected from those noted above in Section (iv) through Section (ix), and at least one required previously known medicament of Section (x) recognized as effective to treat chronic obstructive pulmonary disease, such as, for example, (a) D-penicillamine (Cuprimine, Merck & Co.), dosage range from 25 mg daily to 1.5 gm daily;
(b) 4H-4-phenylthieno-[3,2-c]-[1]-benzopyran-2-carboxylic acid, dosage range from 0.5 mg/kg daily to 50 mg/kg daily;
(c) 4H-2-carboxamido-4-phenylthieno-[3,2-c]-[1]-benzopyran, dosage range from 0.5 mg/kg daily to 50 mg/kg daily;
(d) dexamethasone (Decadron, Merck & Co.), dosage range from 0.1 mg daily to 18 mg daily;
(e) indomethacin (Indocin), dosage range from 25 mg daily to 250 mg daily;
(f) prednisolone (Pediapred, Fisons), dosage range from 1 mg daily or every other day to 250 mg daily;
(g) hydrocortisone, dosage range from 1 mg daily to 400 mg daily;
(h) flurbiprofen (Ansaid), dosage range from 50 mg daily to 500 mg daily;
(i) S-carboxymethylcysteine, dosage range from 1 mg/kg daily to 100 mg/kg daily;
(j) prednisone (Deltasone, Upjohn), dosage range from 1 mg daily to 250 mg daily, or alternate day dosing; and
(k) methylprednisolone, dosage range from 0.25 mg/kg daily to 3 mg/kg daily.

The following illustrate specific formulations according to the present invention.

| | |
|---|---|
| 4-amino-2-methylphenylacetic acid | 1 gm |
| N-acetylcysteine | 500 mg |
| 4H-2-carboxamido-4-phenylthieno-[3,2-c]-[1]-benzopyran | 25 mg |
| p-aminobenzoic acid, potassium salt | 20 gm |
| 2-aminomethyl-4-tert-butyl-6-iodophenol | 20 gm |
| flurbiprofen | 500 mg |
| 4-amino-2-methoxybenzoic acid, potassium salt | 5 gm |
| acetyl-L-carnitine | 1.5 gm |
| methylprednisolone | 50 mg |

Example 15

Clinical treatment of inflammatory myopathies can be improved by use of a composition comprising at least one primary agent of Section (ii), and one or more required substance selected from those noted above in Section (iv) through Section (ix), and at least one required previously known medicament of Section (x) recognized as effective to treat inflammatory myopathies, such as, for example, (a) prednisone (Deltasone, Upjohn), dosage range from 1 mg daily to 250 mg daily, or alternate day dosing;
(b) methotrexate (Rheumatrex, Lederle Laboratories), dosage range from 1 mg weekly to 20 mg weekly;
(c) methotrexate sodium, dosage range from 2.5 mg daily to 30 mg daily, or doses from 5 mg to 50 mg once or twice weekly;
(d) cyclophosphamide, dosage range from 0.1 mg/kg daily to 5 mg/kg daily, 2 mg/kg to 5 mg/kg twice weekly or 10 mg/kg to 15 mg/kg every seven to ten days;
(e) chlorambucil (Leukeran, Burroughs Wellcome), dosage range from 0.5 mg daily to 10 mg daily; and
(f) azathioprine (Imuran, Burroughs Wellcome), dosage range from 0.1 mg/kg daily to 2.5 mg/kg daily; and
(g) diazepam, dosage range from 2 mg daily to 40 mg daily.

The following illustrate specific formulations according to the present invention.

| | |
|---|---|
| 4-(aminoguanidino)benzoic acid | 1 gm |
| ebselen | 250 mg |
| prednisone | 1 mg |
| p-guanidinobenzoic acid, potassium salt | 20 gm |

-continued

| | |
|---|---|
| 5-[[3,5-bis(1,1-dimethylethyl)-4-hydroxyphenyl]-methylene]-3-(dimethylamino)-4-thiazolidinone | 7.5 gm |
| cyclophosphamide | 500 mg |
| 4-amino-2-methoxybenzoic acid, potassium salt | 5 gm |
| acetylhomocysteine thiolactone | 750 mg |
| chlorambucil | 5 mg |

Example 16

Clinical treatment of inflammatory neuropathies can be improved by use of a composition comprising at least one primary agent of Section (ii), and one or more required substance selected from those noted above in Section (iv) through Section (ix), and at least one required previously known medicament of Section (x) recognized as effective to treat inflammatory neuropathies, such as, for example, (a) cortisone (Cortone, Merck & Co.), dosage range from 5 mg daily to 400 mg daily;

(b) prednisone (Deltasone, Upjohn), dosage range from 1 mg daily to 250 mg daily, or alternate day dosing;

(c) methylprednisolone (Medrol, Upjohn), dosage range from 1 mg daily to 250 mg daily, or alternate day dosing;

(d) methylprednisolone acetate, dosage range from 0.5 mg daily to 50 mg daily, or weekly dosage of from 20 mg to 120 mg;

(e) triamcinolone (Aristocort, Fujisawa), dosage range from 1 mg daily to 200 mg daily, or alternate day dosing;

(f) triamcinolone diacetate, dosage range from 1 mg daily to 200 mg daily, or alternate day dosing;

(g) betamethasone, dosage range from 0.1 mg daily to 12 mg daily, or alternate day dosing;

(h) dexamethasone, dosage range from 0.1 mg daily to 18 mg daily;

(i) hydrocortisone (Hydrocortone, Merck & Co.), dosage range from 1 mg daily to 400 mg daily; and (j) prednisolone (Pediapred, Fisons), dosage range from 1 mg daily or every other day to 250 mg daily.

The following illustrate specific formulations according to the present invention.

| | |
|---|---|
| 4-aminocyclohexanecarboxylic acid | 1 gm |
| d-α-tocopheryl acetate | 500 I.U. |
| prednisone | 1 mg |
| p-aminophenylacetic acid, potassium salt | 20 gm |
| 2,6-di-tert-butyl-4-[2'-thenoyl]phenol | 20 gm |
| betamethasone (intramuscular dosage) | 12 mg |
| 4-amino-2-hydroxybenzoic acid | 5 gm |
| L-methionine | 2 gm |
| hydrocortisone | 50 mg |

Example 17

Clinical treatment of myasthenia gravis can be improved by use of a composition comprising from about 1 gm to about 20 gm of at least one primary therapeutic agent comprising a primary amine or amine-related benzoic acid derivative having a molecular weight of from about 100 to about 1,400 Daltons, and at least one required substance selected from those noted above in section (iv) through section (ix), and a medicament recognized as effective to treat myasthenia gravis, such as, for example, (a) prednisone (Deltasone, Upjohn), dosage range from 1 mg daily to 250 mg daily, or alternate day dosing;

(b) azathioprine (Imuran, Burroughs Wellcome), dosage range from 0.1 mg/kg daily to 2.5 mg/kg daily;

(c) pyridostigmine, dosage range from 100 mg daily to 1.5 gm daily;

(d) neostigmine bromide (Prostigmin, ICN), dosage range from 5 mg daily to 375 mg daily;

(e) neostigmine methylsulfate, dosage range from 0.5 mg daily to 10 mg daily;

(f) atropine, dosage range from 0.2 mg daily to 2 mg daily;

(g) propantheline (Pro-Banthine, Schiapparelli Searle), dosage range from 15 mg daily to 75 mg daily; and (h) ephedrine, dosage range from 10 mg daily to 100 mg daily.

The following illustrate specific formulations according to the present invention.

| | |
|---|---|
| 4-amino-2-methylbenzoic acid | 1 gm |
| mixed tocopherols | 500 I.U. |
| pyridostigmine | 100 mg |
| 4-amino-2-methoxybenzoic acid, potassium salt | 15 gm |
| D-myo-inositol-1,2,6-trisphosphate | 20 gm |
| azathioprine | 150 mg |
| 4-(aminoguanidino)phenylacetic acid | 5 gm |
| deferoxamine mesylate | 200 mg |
| propantheline | 25 mg |

Example 18

Clinical treatment of multiple sclerosis can be improved by use of a composition comprising at least one primary agent of Section (ii), and one or more required substance selected from those noted above in Section (iv) through Section (ix), and at least one required previously known medicament of Section (x) recognized as effective to treat multiple sclerosis, such as, for example, (a) 15-deoxyspergualin, dosage range from 0.5 mg/kg daily to 10 mg/kg daily;

(b) leflunomide, dosage range from 50 _g daily to 50 mg daily;

(c) methylprednisolone (Medrol, Upjohn), dosage range from 1 mg daily to 250 mg daily, or alternate day dosing;

(d) prednisone (Deltasone, Upjohn), dosage range from 1 mg daily to 250 mg daily, or alternate day dosing;

(e) dexamethasone (Decadron, Merck & Co.), dosage range from 0.1 mg daily or every other day to 10 mg daily or every other day;

(f) corticotropin, dosage range from from 10 units daily to 150 units daily;

(g) cyclosporin A (Sandimmune, Sandoz Pharmaceutical), dosage range from 1 mg/kg daily to 15 mg/kg daily;

(h) amantadine (Symmetrel, Du Pont Multi-Source Products), dosage range from 10 mg daily to 400 mg daily;

(i) diazepam (Valium, Roche Products), dosage range from 0.5 mg daily to 40 mg daily;

(j) clonazepam (Klonopin, Roche Laboratories), dosage range from 0.5 mg daily to 20 mg daily;

(k) carbamazepine (Tegretol, Geigy), dosage-range from 40 mg daily to 1.6 gm daily;

(l) phenytoin (Dilantin-125, Parke-Davis), dosage range from 50 mg daily to 625 mg daily;

(m) isoniazid (INH isoniazid, CIBA), dosage range from 10 mg daily to 300 mg daily;

(n) primidone (Mysoline, Wyeth-Ayerst Laboratories), dosage range from 25 mg daily to 1.75 gm daily;

(o) propranolol (Inderal, Wyeth-Ayerst Laboratories), dosage range from 30 mg daily to 640 mg daily;

(p) amitriptyline (Elavil, Stuart), dosage range from 50 mg daily to 300 mg daily;

(q) oxybutynin (Ditropan, Marion Merrell Dow), dosage range from 2.5 mg daily to 20 mg daily;

(r) propantheline (Pro-Banthine, Schiapparelli Searle), dosage range from 2.5 mg daily to 75 mg daily;

(s) imipramine, dosage range from 2 mg daily to 150 mg daily;

(t) carbachol, dosage range from 50 μg/kg daily to 5 mg/kg daily;

(u) bethanechol (Urecholine, Merck & Co.), dosage range from 5 mg daily to 200 mg daily;

(v) phenoxybenzamine (Dibenzyline, SmithKline Beecham), dosage range from 5 mg daily to 150 mg daily;

(w) tizanidine, dosage range from 50 _g/kg daily to 5 mg/kg daily;

(x) chlorpromazine (Thorazine, SmithKline Beecham), dosage range from 10 mg daily to 200 mg daily;

(y) baclofen (Atrofen, Athena Neurosciences), dosage range from 1 mg daily to 80 mg daily;

(z) diacetylrhein, dosage range from 10 mg daily to 500 mg daily;

(a') alfa-2a interferon, dosage range from 300,000 IU daily to 36,000,000 IU daily;

(b') alfa-2b interferon, dosage range from 300,000 IU daily to 5,000,000 IU daily;

(c') alfa-N3 interferon, dosage range from 250,000 IU daily to 2,500,000 IU daily;

(d') beta interferon, dosage range from 5,000 U/kg daily to 50,000 U/kg daily;

(e') gamma-1b interferon, dosage range from 5,000 U/kg daily to 50,000 U/kg daily;

(f') copolymer-1 (random polymer of L-alanine, L-glutamic acid, L-lysine and L-tyrosine, ratio of 6.0:1.9:4.7:1.0, of molecular weight between 14,000 and 23,000 Daltons), dosage range 2 mg daily to 40 mg daily;

(g') 4-aminopyridine, dosage range from 0.25 mg/kg daily to 10 mg/kg daily;

(h') 3,4-diaminopyridine, dosage range from 50 μg daily to 100 mg daily;

(i') cyclophosphamide (Cytoxan, Bristol-Myers Oncology), dosage range from 0.1 mg/kg daily to 5 mg/kg daily;

(j') prednisolone (Pediapred, Fisons), dosage range from 1 mg daily or every other day to 250 mg daily;

(k') methylprednisolone acetate, dosage range from 0.5 mg daily to 50 mg daily, or weekly dosage of from 20 mg to 120 mg;

(l') triamcinolone (Aristocort, Fujisawa), dosage range from 1 mg daily to 200 mg daily, or alternate day dosing;

(m') triamcinolone diacetate, dosage range from 1 mg daily to 200 mg daily, or alternate day dosing;

(n') methylprednisolone, dosage range from 0.25 mg/kg daily to 3 mg/kg daily; and (o') azathioprine (Imuran, Burroughs Wellcome), dosage range from 5 mg daily to 300 mg daily.

The following illustrate specific formulations according to the present invention.

| | |
|---|---|
| 4-guanidino-2-methylbenzoic acid | 1 gm |
| prostaglandin B₁ oligomers | 300 mg |
| diacetylrhein | 10 mg |
| 4-amino-2-hydroxybenzoic acid | 20 gm |
| N,N'-dimethylthiourea | 5 gm |

-continued

| | |
|---|---|
| baclofen | 80 mg |
| 4-(aminoguanidino)-2-methoxyphenylacetic acid | 5 gm |
| N,N'-diphenyl-p-phenylenediamine | 10 gm |
| carbamazepine | 500 mg |

Example 19

Clinical treatment of epilepsy can be improved by use of a composition comprising at least one primary agent of Section (ii), and one or more required substance selected from those noted above in Section (iv) through Section (ix), and at least one required previously known medicament of Section (x) recognized as effective to treat epilepsy, such as, for example, (a) dizocilpine (Neurogard, Merck Sharp & Dohme), dosage range from 0.1 μg/kg daily to 10 mg/kg daily;

(b) phenytoin (Dilantin-125, Parke-Davis), dosage range from 50 mg daily to 625 mg daily;

(c) phenytoin-polyvinylpyrrolidone coprecipitate, dosage range from 50 mg daily to 1 gm daily;

(d) phenytion in combination with phenobarbital (Dilantin capsules, Parke-Davis), dosage range from 100 mg phenytoin sodium and 16 mg phenobarbital daily to 600 mg phenytoin sodium and 192 mg phenobarbital daily;

(e) phenobarbital (Lilly), dosage range from 5 mg daily to 200 mg daily;

(f) primidone (Mysoline, Wyeth-Ayerst Laboratories), dosage range from 25 mg daily to 1.75 gm daily;

(g) carbamazepine (Tegretol, Basel), dosage range from 50 mg daily to 1.2 gm daily;

(h) ethosuximide (Zarontin, Parke-Davis), dosage range from 250 mg daily to 2 gm daily;

(i) clonazepam (Klonopin, Roche Laboratories), dosage range from 0.5 mg daily to 20 mg daily;

(j) valproic acid (Depakene, Abbott Laboratories), dosage range from 1 mg/kg daily to 60 mg/kg daily;

(k) divalproex sodium (Depakote, Abbott Laboratories), dosage range from 1 mg/kg daily to 60 mg/kg daily;

(l) acetazolamide (Diamox, Lederle), dosage range from 50 mg daily to 2 gm daily;

(m) acetazolamide sodium, dosage range from 50 mg daily to 2 gm daily;

(n) prednisone (Deltasone, Upjohn), dosage range from 1 mg daily to 250 mg daily, or alternate day dosing;

(o) corticotropin, dosage range from 5 units daily to 60 units daily;

(p) diazepam (Valium, Roche Products), dosage range from 2 mg daily to 40 mg daily;

(q) lorazepam, dosage range from 50 μg/kg daily to 300 μg/kg daily;

(r) felbamate, dosage range from 100 _g/kg daily to 2 mg/kg daily;

(s) zonisamide, dosage range from 100 _g/kg daily to 2 mg/kg daily;

(t) gabapentin (Neurontin, Warner-Lambert), dosage range from 100 μg/kg daily to 2 mg/kg daily;

(u) lamotrigine (Lamictal, Burroughs Wellcome), dosage range from 100 μg/kg daily to 2 mg/kg daily; and (v) vigabatrin (Sabril, Marion Merrell Dow), dosage range from 100 pg/kg daily to 2 mg/kg daily.

The following illustrate specific formulations according to the present invention.

| | |
|---|---|
| 5-amino-2-hydroxybenzoic acid | 1 gm |
| d-α-tocopheryl succinate | 750 I.U. |
| phenytoin | 50 mg |
| p-aminobenzoic acid | 10 gm |
| ebselen | 10 gm |
| dizocilpine | 500 mg |
| 4-aminophenylacetic acid | 5 gm |
| prostaglandin $B_1$ oligomers | 7.5 gm |
| primidone | 1 gm |

Example 20

Clinical treatment of inflammatory site edema can be improved by use of a composition comprising at least one primary agent of Section (ii), and one or more required substance selected from those noted above in Section (iv) through Section (ix), and at least one required previously known medicament of Section (x) recognized as effective to treat inflammatory site edema, such as, for example, (a) cyproheptadine, dosage range from 5 mg/kg daily to 50 mg/kg daily;

(b) clemastine, dosage range from 20 mg/kg daily to 200 mg/kg daily;

(c) setastine, dosage range from 20 mg/kg daily to 200 mg/kg daily;

(d) indomethacin, dosage range from 1 mg/kg daily to 100 mg/kg daily;

(e) piroxicam, dosage range from 20 mg/kg daily to 200 mg/kg daily;

(f) phenylbutazone, dosage range from 50 mg/kg daily to 500 mg/kg daily;

(g) dexamethasone, dosage range from 0.1 mg daily to 18 mg daily;

(h) phenidone, dosage range from 25 mg/kg daily to 1 gm/kg daily;

(i) nordihydroguaiaretic acid, dosage range from 100 mg/kg daily to 2 gm/kg daily;

(j) ketoconazole, dosage range from 100 mg/kg daily to 2 gm/kg daily;

(k) suprofen, dosage range from 5 mg/kg daily to 100 mg/kg daily;

(l) ketoprofen, dosage range from 2 mg/kg daily to 50 mg/kg daily;

(m) indoprofen, dosage range from 1 mg/kg daily to 30 mg/kg daily;

(n) sudoxicam, dosage range from 0.5 mg/kg daily to 40 mg/kg daily;

(o) naproxen, dosage range from 1 mg/kg daily to 100 mg/kg daily;

(p) meclofenamic acid, dosage range from 15 mg/kg daily to 150 mg/kg daily;

(q) ibuprofen, dosage range from 15 mg/kg daily to 150 mg/kg daily;

(r) diclofenac, dosage range from 1 mg/kg daily to 25 mg/kg;

(s) fenoprofen, dosage range from 5 mg/kg daily to 100 mg/kg daily;

(t) hydroxychloroquine, dosage range from 20 mg/kg daily to 400 mg/kg daily;

(u) 2,6-diamino-N-{[1-(1-oxotridecyl)-2-piperidinyl]-methyl}-hexanamide, dosage range from 0.5 mg/kg daily to 50 mg/kg daily;

(v) bucloxic acid, dosage range from 200 mg daily to 2 gm daily;

(w) butibufen, dosage range from 40 mg/kg daily to 400 mg/kg daily;

(x) carprofen, dosage range from 0.2 mg/kg daily to 50 mg/kg daily;

(y) the (S)(+) enantiomer of carprofen, dosage range from 50 mg daily to 750 mg daily;

(z) 6-(2,4-difluorophenoxy)-5-methylsulfonylamino-1-indanone (Ciba-Geigy AG), dosage range from 0.2 mg/kg daily to 20 mg/kg daily;

(a') loxoprofen, dosage range from 0.1 mg/kg daily to 25 mg/kg daily;

(b') diaveridine, dosage range from 25 mg/kg daily to 500 mg/kg daily;

(c') ditazol, dosage range from 25 mg/kg daily to 750 mg daily;

(d') droxicam, dosage range from 0.1 mg/kg daily to 50 mg/kg daily;

(e') (Z)-3-[4-(acetyloxy)-5-ethyl-3-methoxy-1-naphthalenyl]-2-methyl-2-propenoic acid, dosage range from 10 mg/kg daily to 500 mg/kg daily;

(f') 1-p-chlorobenzyl-2-dimethyl-aminomethylcyclohexen-1,2, dosage range from 2.5 mg/kg daily to 250 mg/kg daily;

(g') etoclofene, dosage range from 1 mg/kg daily to 400 mg/kg daily;

(h') flufenamic acid, dosage range from 1 mg/kg daily to 400 mg/kg daily;

(i') benzydamine, dosage range from 10 mg/kg daily to 1 gm/kg daily;

(j') mefenamic acid, dosage range from 1 mg/kg daily to 400 mg/kg daily;

(k') fenbufen, dosage range from 250 mg daily to 1.25 gm daily;

(l') felbinac, dosage range from 100 mg daily to 1.25 gm daily;

(m') fenclorac, dosage range from 0.5 mg/kg daily to 50 mg/kg daily;

(n') fenclozic acid, dosage range from 25 mg daily to 500 mg daily;

(o') fendosal, dosage range from 5 mg/kg daily to 200 mg/kg daily;

(p') isoxepac, dosage range from 200 mg daily to 2 gm daily;

(q') imidazole salicylate, dosage range from 50 _mol/kg daily to 0.5 mmol/kg daily;

(r') isoxicam, dosage range from 50 mg daily to 500 mg daily;

(s') tolmetin, dosage range from 50 mg daily to 500 mg daily;

(t') leflunomide, dosage range from 50 _g daily to 50 mg daily;

(u') isofezolac, dosage range from 0.1 mg/kg daily to 25 mg/kg daily;

(v') 1-isobutyl-3,4-diphenylpyrazole-5-acetic acid, dosage range from 0.5 mg/kg daily to 50 mg/kg daily;

(w') S-adenosylmethionine, dosage range from 500 mg daily to 10 gm daily;

(x') D-myo-inositol-1.2.6-trisphosphate, dosage range from 10 mg/kg daily to 1.5 gm daily;

(y') diacetylrhein, dosage range from 10 mg daily to 500 mg daily;

(z') cinmetacin, dosage range from 2 mg/kg daily to 400 mg/kg daily;

(a") tinoridine, dosage range from 2.5 mg/kg daily to 250 mg/kg daily;

(b") nimesulide, dosage range from 100 mg daily to 2 gm daily;

(c") prenazone, dosage range from 0.5 mg/kg daily to 400 mg/kg daily;

(d") naphthypramide, dosage range from 0.5 mg/kg daily to 400 mg/kg daily;

(e") perisoxal, dosage range from 0.5 mg/kg daily to 400 mg/kg daily;

(f") proquazone, dosage range from 150 mg daily to 1.5 gm daily;

(g") ketorolac, dosage range from 20 µg/kg daily to 2 mg/kg daily;

(h") hydrocortisone (Hydrocortone, Merck & Co.), dosage range from 1 mg daily to 400 mg daily;

(i") prednisolone (Pediapred, Fisons), dosage range from 1 mg daily or every other day to 250 mg daily;

(j") cortisone (Cortone, Merck & Co.), dosage range from 5 mg daily to 400 mg daily;

(k") prednisone (Deltasone, Upjohn), dosage range from 1 mg daily to 250 mg daily, or alternate day dosing;

(l") methylprednisolone (Medrol, Upjohn), dosage range from 1 mg daily to 250 mg daily, or alternate day dosing;

(m") methylprednisolone acetate, dosage range from 0.5 mg daily to 50 mg daily, or weekly dosage of from 20 mg to 120 mg;

(n") triamcinolone (Aristocort, Fujisawa), dosage range from 1 mg daily to 200 mg daily, or alternate day dosing;

(o") triamcinolone diacetate, dosage range from 1 mg daily to 200 mg daily, or alternate day dosing;

(p") betamethasone (Celestone, Schering), dosage range from 0.2 mg daily to 12 mg daily, or alternate day dosing; and (q") N,N'-diphenyl-p-phenylenediamine, dosage range from 10 mg/kg daily to 250 mg/kg daily.

The following illustrate specific formulations according to the present invention.

| | |
|---|---|
| 4-guanidinocyclohexanecarboxylic acid | 1 gm |
| N-acetylcysteine | 750 mg |
| cyproheptadine | 300 mg |
| p-aminobenzoic acid, potassium salt | 15 gm |
| ebselen | 20 gm |
| S-adenosylmethionine | 10 gm |
| 4-(aminoguanidino)-2-methoxybenzoic acid | 5 gm |
| deferoxamine mesylate | 500 mg |
| meclofenamic acid | 5 gm |

Example 21

Clinical treatment of post-event ischemia and reperfusion symptomology resulting from acute central nervous system trauma, including stroke and spinal cord trauma can be improved by use of a composition comprising at least one primary agent of Section (ii), and one or more required substance selected from those noted above in Section (iv) through Section (ix), and at least one required previously known medicament of Section (x) recognized as effective to treat post-event ischemia and reperfusion symptomology resulting from acute central nervous system trauma, including stroke and spinal cord trauma, such as, for example, (a) heparin calcium, dosage range from 5,000 units daily to 40,000 units daily;

(b) heparin sodium, dosage range from 5,000 units daily to 40,000 units daily;

(c) warfarin (Coumadin, Du Pont), dosage range from 1 mg daily to 15 mg daily;

(d) ticlopidine (Ticlid, Syntex), dosage range from 50 mg daily to 750 mg daily;

(e) aminophylline, dosage range from 5 mg/kg daily to 75 mg/kg daily;

(f) isoproterenol, dosage range from 10 µg daily to 1 mg daily;

(g) methohexital sodium, dosage range from 5 mg/kg/hr to 50/kg/hr post-trauma;

(h) tirilazad mesylate (U-74006F), dosage range from 150 µg/kg/hr to 15 mg/kg/hr;

(i) derivative of tirilazad in which the steroid portion of the chemical structure has been replaced with the tetramethyl chroman portion of d-α tocopherol (U78517F, Upjohn), dosage range from 150 µg/kg/hr to 15 mg/kg/hr;

(j) allopurinol (Zyloprim, Burroughs Wellcome), dosage range from 50 mg daily to 800 mg daily;

(k) methylprednisolone, dosage range from 5 µg/kg daily to 0.1 mg/kg daily or immediate post-event treatment dosage range from 30 mg/kg to 160 mg/kg during a 24 hour period;

(l) moclobemide (Aurorix, Hoffmann-La Roche), dosage range from 50 mg daily to 600 mg daily;

(m) sulfinpyrazone (Anturane, CIBA), dosage range from 50 mg daily to 800 mg daily;

(n) dipyridamole (Persantine, Boehringer Ingelheim), dosage range from 25 mg daily to 400 mg daily;

(o) clofibrate (Atromid-S, Wyeth-Ayerst Laboratories), dosage range from 100 mg daily to 2 gm daily; and (p) N-methyl-D-aspartate glutamate receptor antagonists administered orally such as trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 µg/kg daily to 10 mg/kg daily;

amantadine (Symmetrel, Du Pont Multi-Source Products), dosage range from 10 mg daily to 400 mg daily;

memantine, dosage range from 10 mg daily to 400 mg daily;

milacemide, dosage range from 50 mg daily to 2.5 grams daily; and dextrorphan (Roche), dosage range from 10 mg daily to 400 mg daily; and (q) low molecular weight sulphate/dermatan sulphate glycoaminoglycan heparinoid mixtures, 6,500 Dalton mean molecular weight, dosage range from 250 anti-factor-Xa units daily to 10,000 antifactor-Xa units daily.

The following illustrate specific formulations according to the present invention.

| | | |
|---|---|---|
| 4-aminocyclohexanecarboxylic acid | 1 | gm |
| deferoxamine mesylate | 500 | mg |
| heparin calcium | 5,000 | units |
| p-aminobenzoic acid | 15 | gm |
| d-α-tocopheryl succinate | 3,500 | I.U. |
| ebselen | 20 | gm |
| methylprednisolone | 5 | mg |
| 4-aminophenylacetic acid | 5 | gm |
| ebselen | 10 | gm |
| moclobemide | 250 | mg |

Example 22

Clinical treatment of post-event consequences of kidney ischemia and reperfusion can be improved by use of a composition comprising at least one primary agent of Section (ii), and one or more required substance selected from those noted above in Section (iv) through Section (ix), and at least one required previously known medicament of Section (x) recognized as effective to treat post-event consequences of kidney ischemia and reperfusion, such as, for example, (a) trimetazidine, dosage range from 100 µg/kg daily to 3.0 mg/kg daily;

(b) allopurinol (Zyloprim, Burroughs Wellcome), dosage range from 50 mg daily to 800 mg daily;

(c) bucloxic acid, dosage range from 200 mg daily to 2 gm daily;

(d) indometacin, dosage range from 25 mg daily to 300 mg daily;

(e) methylprednisolone (Medrol, Upjohn), dosage range from 1 mg daily to 250 mg daily, or alternate day dosing;

(f) prednisone (Deltasone, Upjohn), dosage range from 1 mg daily to 250 mg daily, or alternate day dosing;

(g) cyclophosphamide (Cytoxan, Bristol-Myers Oncology), dosage range from 0.1 mg/kg daily to 5 mg/kg daily;

(h) chlorambucil (Leukeran, Burroughs Wellcome), dosage range from 0.5 mg daily to 10 mg daily;

(i) cyclosporin A (Sandimmune, Sandoz Pharmaceutical), dosage range from 1 mg/kg daily to 15 mg/kg daily;

(j) azathioprine (Imuran, Burroughs Wellcome), dosage range from 0.1 mg/kg daily to 2.5 mg/kg daily; and (k) N,N'-diphenyl-p-phenylenediamine, dosage range from 10 mg/kg daily to 250 mg/kg daily.

The following illustrate specific formulations according to the present invention.

| | |
|---|---|
| 4-amino-2-hydroxyphenylacetic acid | 1 gm |
| nordihydroguaiaretic acid | 5 gm |
| trimetazidine | 7.5 mg |
| p-aminobenzoic acid | 15 gm |
| mixed tocopherols | 3,500 I.U. |
| N,N'-diphenyl-p-phenylenediamine | 15 gm |
| 4-(aminoguanidino)phenylacetic acid | 5 gm |
| D-myo-inositol-1.2.6-trisphosphate | 20 gm |
| ebselen | 5 gm |
| cyclophosphamide | 200 mg |

Example 23

Clinical treatment of post-event consequences of reperfusion subsequent to myocardial infarction can be improved by use of a composition comprising at least one primary agent of Section (ii), and one or more required substance selected from those noted above in Section (iv) through Section (ix), and at least one required previously known medicament of Section (x) recognized as effective to treat post-event consequences of reperfusion sub-sequent to myocardial infarction, such as, for example, (a) trimetazidine, dosage range from 100 µg/kg daily to 3.0 mg/kg daily;

(b) allopurinol (Zyloprim, Burroughs Wellcome), dosage range from 50 mg daily to 800 mg daily;

(c) lidocaine, dosage range from 0.5 mg/kg to 1 mg/kg until ectopy resolves;

(d) procainamide (Procan SR extended-release tablets, Parke-Davis), dosage range from 200 mg daily to 5 gm daily;

(e) β-adrenoceptor blockers such as acebutolol (Sectral), dosage range from 20 mg daily to 1.2 gm daily;

alprenolol, dosage range from 0.5 mg/kg daily to 5 mg/kg daily; atenolol (Tenormin), dosage range from 2.5 mg daily to 200 mg daily;

betaxolol (Kerlone), dosage range from 1 mg daily to 20 mg daily;

carteolol (Cartrol), dosage range from 0.25 mg daily to 10 mg daily;

esmolol, dosage range from 50 µg/kg/min to 0.2 mg/kg/min;

labetalol (Normodyne), dosage range from 20 mg daily to 1.8 gm daily;

metoprolol (Lopressor), dosage range from 5 mg daily to 200 mg daily;

nadolol (Corgard), dosage range from 4 mg daily to 240 mg daily;

oxprenolol, dosage range from 0.5 mg/kg daily to 5 mg/kg daily;

penbutolol (Levatol), dosage range from 2 mg daily to 80 mg daily;

pindolol (Visken), dosage range from 0.5 mg daily to 60 mg daily;

propranolol (Inderal or Inderal LA), dosage range from 4 mg daily to 320 mg daily;

sotalol (Betapace, Berlex), dosage range from 30 mg daily to 320 mg daily; and timolol (Blocadren), dosage range from 1 mg daily to 60 mg daily; (f) nitrates such as sodium nitroprusside, intravenous dosage range from 1 mg daily to 100 mg daily;

isosorbide 5-mononitrate, dosage range from 10 mg daily 100 mg daily;

isosorbide dinitrate, dosage range from 2 mg daily to 240 mg daily; and sustained-release trinitroglycerin, dosage range from 1 mg daily to 540 mg daily;

(g) calcium antagonists such as diltiazem (Cardizem or Cardizem SR), dosage range from 10 mg daily to 360 mg daily;

verapamil (Calan or Calan SR), dosage range from 10 mg to 480 mg;

nifedipine (Procardia), dosage range from 3 mg daily to 180 mg daily;

nifedipine (Procardia XL), dosage range from 3 mg daily to 90 mg daily;

nicardipine (Cardene), dosage range from 6 mg daily to 120 mg daily;

isradipine (DynaCirc), dosage range from 0.5 mg daily to 20 mg daily;

amlodipine (Norvasc, Pfizer Labs Division), dosage range from 0.5 mg daily to 10 mg daily; and felodipine (Plendil, Merck & Co.), dosage range from 0.5 mg daily to 20 mg daily;

(h) N,N'-dimethylthiourea, dosage range from 5 mg/kg daily to 100 mg/kg daily;

(i) N-2-mercaptopropionylglycine, dosage range from 5 mg/kg daily to 100 mg/kg daily;

(j) deferoxamine mesylate, dosage range from 1 mg/kg daily to 50 mg/kg daily;

(k) taurine, dosage range from 1 mg/kg daily to 100 mg/kg daily;

(l) heparin, dosage range 10,000 units/day to 25,000 units/day; and (m) angiotensin converting enzyme inhibitors including captopril (Capoten), dosage range from 2.5 mg daily to 300 mg daily;

enalapril (Vasotec), dosage range from 0.25 mg daily to 40 mg daily;

fosinopril (Monopril), dosage range from 1 mg daily to 60 mg daily;

lisinopril (Zestril), dosage range from 0.5 mg daily to 40 mg daily;

ramipril (Altace), dosage range from 0.25 mg daily to 10 mg daily;

quinapril (Accupril, Parke-Davis), dosage range from 1 mg daily to 80 mg daily;

quinapril/hydrochlorothiazide combinations (Accuretic, Parke-Davis), dosage range from 2 mg quinapril and 1.25 mg hydrochloro-thiazide daily to 80 mg quinapril and 125 mg hydrochlorothiazide daily; and benazepril (Lotensin, CIBA Pharmaceutical), dosage range from 0.1 mg daily to 80 mg daily.

The following illustrate specific formulations according to the present invention.

| | |
|---|---|
| 4-amino-2-methoxyphenylacetic acid | 1 gm |
| butylated-hydroxytoluene | 200 mg |
| allopurinol | 200 mg |
| p-aminobenzoic acid | 20 gm |
| tert-butylhydroquinone | 1 gm |
| isosorbide 5-mononitrate | 100 mg |
| 4-aminophenylacetic acid | 10 gm |
| 2,6-di-tert-butyl-4-[2'-thenoyl]phenol | 500 mg |
| captopril | 200 mg |

Example 24

Use of agents previously recognized as having general anti-inflammatory properties and as possibly having usefulness in clinically treating chronic inflammatory diseases of varying origin, but which at present remain under investigation can be improved by use of a composition comprising at least one primary agent of Section (ii), and one or more required substance selected from those noted above in Section (iv) through Section (ix), and at least one required previously known medicament of Section (x), said required previously known medicament being an agent previously recognized as having general anti-inflammatory properties and as possibly having usefulness in clinically treating chronic inflammatory diseases of varying origin, but which at present remain under investigation, such as, for example, (a) tilomisole (WY-18,251, NSC-310,663), dosage range from 0.1 mg/kg daily to 100 mg/kg daily;

(b) tenidap, dosage range from 0.1 mg/kg daily to 100 mg/kg daily;

(c) 1-[(4-chlorophenyl)methyl]-2-methyl-5-(quinolinylmethoxy)-1H-indole-3-acetic acid, dosage range from 0.1 mg/kg daily to 100 mg/kg daily;

(d) tepoxalin, dosage range from 0.1 mg/kg daily to 100 mg/kg daily;

(e) scalaradial, dosage range from 0.1 mg/kg daily to 100 mg/kg daily;

(f) tirilazad mesylate (U-74006F), dosage range from 0.15 mg/kg/hr to 15 mg/kg/hr;

(g) derivative of tirilazad in which the steroid portion of the chemical structure has been replaced with the tetramethyl chroman portion of d-α tocopherol (U78517F, Upjohn), dosage range from 150 μg/kg/hr to 15 mg/kg/hr;

(h) pentoxifylline (Hoechst-Roussell Pharmaceuticals), dosage range from 1 mg/kg daily to 100 mg/kg;

(i) indoxole, dosage range from 0.5 mg/kg daily to 50 mg/kg daily;

(j) bimetopyrol, dosage range from 0.5 mg/kg daily to 50 mg/kg daily;

(k) flumizole, dosage range from 0.5 mg/kg daily to 50 mg/kg daily;

(l) phenidone, dosage range from 25 mg/kg daily to 1 gm/kg daily;

(m) bucolome, dosage range from 200 mg daily to 2 gm daily;

(n) sodium 2-[4-(2-oxocyclopentylmethyl)phenyl]propionate dihydrate, dosage range from 0.1 mg/kg daily to 25 mg/kg daily;

(o) sideritoflavone, dosage range from 50 mg/kg daily to 1 gm daily;

(p) cirsiliol, dosage range from 50 mg/kg daily to 1 gm daily;

(q) hypolaetin-8-glucoside, dosage range from 50 mg/kg daily to 1 gm daily;

(r) hypolaetin, dosage range from 50 mg/kg daily to 1 gm daily;

(s) oroxindin, dosage range from 50 mg/kg daily to 1 gm daily;

(t) quercetagetin-7-glucoside, dosage range from 50 mg/kg daily to 1 gm daily;

(u) gossypin, dosage range from 50 mg/kg daily to 1 gm daily;

(v) hibifolin, dosage range from 50 mg/kg daily to 1 gm daily;

(w) gossypetin, dosage range from 50 mg/kg daily to 1 gm daily;

(x) leucocyanidol, dosage range from 50 mg/kg daily to 1 gm daily;

(y) indoprofen, dosage range from 0.5 mg/kg daily to 50 mg/kg daily;

(z) 1-[3-(naphth-2-ylmethoxy)phenyl]-1-(thiazol-2-yl)propyl methyl ether, dosage range from 1 mg/kg daily to 100 mg/kg daily;

(a') epirizole, dosage range from 5 mg/kg daily to 150 mg/kg daily;

(b') DL-2-(4-hexyloxyphenyl)glycine octyl ester, dosage range from 25 mg daily to 500 mg daily;

(c') DL-2-[4-(5.5-dimethylhexyloxy)phenyl]glycine octyl ester, dosage range from 25 mg daily to 500 mg daily;

(d') meloxicam, dosage range from 0.1 mg/kg daily to 50 mg/kg daily;

(e') kojic acid, dosage range from 0.1 mg/kg daily to 50 mg/kg daily;

(f') 2-(2-hydroxy-4-methylphenyl)aminothiazole hydrochloride, dosage range from 0.1 mg/kg daily to 50 mg/kg daily;

(g') 2-(p-bromophenyl)-9-dimethylaminopropyl-9H-imidazo[1,2-α]-benzimidazole, dosage range from 0.1 mg/kg daily to 50 mg/kg daily;

(h') benoxaprofen, dosage range from 0.1 mg/kg daily to 50 mg/kg daily;

(i') flunoxaprofen, dosage range from 0.1 mg/kg daily to 50 mg/kg daily;

(i') emorfazone, dosage range from 0.1 mg/kg daily to 100 mg/kg daily;

(k') misoprostol, dosage range from 10 _g/k daily to 1 mg/kg daily;

(l') 6-methoxy-2-naphthylacetic acid, dosage range from 1 mg/kg daily to 100 mg/kg daily;

(m') niflumic acid, dosage range from 250 mg daily to 5 gm daily;

(n') clidanac, dosage range from 0.1 mg/kg daily to 100 mg/kg daily;

(o') proglumetacin, dosage range from 0.5 mg/kg daily to 200 mg/kg daily;

(p') 4-(2-chlorophenyl)-2-[2-(4-isobutylphenyl)ethyl]-6,9-dimethyl-6H-thieno[3,2-f][1,2,4]triazolo[4,3a][1,4]diazepine (Y-24180), dosage range from 10 μg/kg daily to 10 mg/kg daily;

(q') paramethasone, dosage range from 1 mg daily to 200 mg daily, or alternate day dosing;

(r') paramethasone 21-acetate, dosage range from 1 mg daily to 200 mg daily, or alternate day dosing; and (s') paramethasone disodium phosphate, dosage range from 1 mg daily to 200 mg daily, or alternate day dosing.

The following illustrate specific formulations according to the present invention.

| | |
|---|---|
| 4-aminophenylacetic acid, potassium salt | 1 gm |
| N-acetylcysteine | 1 gm |
| tenidap | 10 mg |
| 4-amino-2-methoxybenzoic acid | 20 gm |
| d-α-tocopheryl succinate | 3,000 I.U. |
| paramethasone 21-acetate | 50 mg |
| 4-aminophenylacetic acid | 15 gm |
| zinc carnosine | 70 mg |
| tilomisole | 2 gm |

Without further elaboration the foregoing will so fully illustrate my invention that others may, by applying current or future knowledge, adapt the same for use under various conditions of service.

The invention claimed is:

1. An orally administered composition comprising:
(a) a therapeutically effective amount of a pharmaceutically acceptable salt form, the free acid form, a pharmaceutically acceptable ester derivative form, or a pharmaceutically acceptable amide derivative form of at least one required primary agent of the formula:

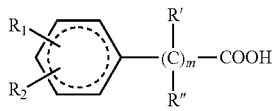

wherein $R_1$ is —$NH_2$; -aminoalkyl having 1-10 carbons; —NHC(=NH)$NH_2$; —$(CH_2)_n$NHC(=NH)$NH_2$ wherein n is 1-10; —C(=NH)$NH_2$; —$(CH_2)_n$—CH=NC(=NH)$NH_2$ wherein n is 1-10; —NHC(=NH)$NHNH_2$; —$(CH_2)_n$NHC(=NH)$NHNH_2$ wherein n is 1-10; —$(CH_2)_n$—CH=NC(=NH)$NHNH_2$ wherein n is 1-10; —NHNHC(=NH)$NH_2$; —$(CH_2)_n$—NHNHC(=NH)$NH_2$ wherein n is 1-10; and —$(CH_2)_n$—CH=N—NHC(=NH)$NH_2$ wherein n is 1-10; $R_2$ is H; —OH; —O—$CH_3$; —O—R' wherein R' is alkyl of 2-10 carbons; aminoalkyl wherein the alkyl group is 1-10 carbons; —$SO_3$H; —$CH_3$; and —$(CH_2)_n$$CH_3$ wherein n is 1-10; R' and R" are —H, —OH or —$CH_3$; and m is 0 or 1;
(b) a therapeutically effective amount of at least one additional required co-agent from the group consisting of
nonabsorbable primary amine polymeric co-agents in a microfibrillated form or microcrystalline form selected from the group consisting of
a. chemically aminated polysaccharides selected from the group consisting of: aminoalkyl-, amino(hydroxyalkyl)-, aminoalkyl-ether-, and amino(hydroxyalkyl)-ether-derivatives of cellulose, chitin and other naturally occurring non-digestible carbohydrates selected from the group consisting of $H_2N$—$(CH_2)_n$-[carbohydrate] where n=1-10;
$H_2N$—$(CH_2)_m$—CHOH—$(CH_2)_n$-[carbohydrate], where m=0-10 and n=0-10;
$H_2N$—$(CH_2)_n$—O—[carbohydrate] where n=1-10;
$H_2N$—$(CH_2)_m$—CHOH—$(CH_2)_n$—O-[carbohydrate] where m=0-10 and, n=0-10;
aminobenzyl-derivatives of cellulose, chitin or other naturally occurring non-digestible carbohydrates selected from the group consisting of $H_2N$—$C_5H_4$-$(CH_2)_n$-[carbohydrate],
$H_2N$—$CH_2$—$C_6H_4$—$(CH_2)_n$-[carbohydrate],
$H_2N$—$C_6H_4$—$(CH_2)_n$—O—[carbohydrate] where n=0-10, and
$H_2N$—$C_6H_4$—$(CH_2)_n$—CHOH—$(CH_2)_n$—O-[carbohydrate] where m=0-10 and n=0-10, including p-, o- and m-benzene ring amino- and aminomethyl-isomers, and alkyl group isomers;
guanidine and aminoguanidine derivatives of cellulose, chitin or other naturally occurring nonabsorbable carbohydrates selected from the group consisting of:
$H_2N$—C(=NH)-[carbohydrate];
$H_2N$—C(=NH)—$(CH_2)_n$-[carbohydrate], where n=1-10, including hydrocarbon isomers and hydroxylated derivatives thereof;
$H_2N$—C(=NH)—O—$(CH_2)_n$-[carbohydrate], where n=1-10, including hydrocarbon isomers, ether linkage isomers and hydroxylated derivatives thereof;
$H_2N$—C(=NH)—NH-[carbohydrate];
$H_2N$—C(=NH)—NH—$(CH_2)_n$-[carbohydrate], where n=1-10, including hydrocarbon isomers and hydroxylated derivatives thereof;
$H_2N$—C(=NH)—NH—$(CH_2)_n$—O—[carbohydrate], where n=1-10, including hydrocarbon isomers, ether linkage isomers and hydroxylated derivatives thereof;
$H_2N$—C(=NH)—N=CH—$(CH_2)_n$-[carbohydrate], where n=1-10, including hydrocarbon isomers and hydroxylated derivatives thereof;
$H_2N$—C(=NH)—N=CH—$(CH_2)_n$—O—[carbohydrate], where n=1-10, including hydrocarbon isomers and hydroxylated derivatives thereof;
$H_2N$—NHC(=NH)—NH-[carbohydrate];
$H_2N$—NHC(=NH)—NH—$(CH_2)_n$-[carbohydrate], where n=1-10, including hydrocarbon isomers and hydroxylated derivatives thereof;
$H_2N$—NHC(=NH)—NH—$(CH_2)_n$—O—[carbohydrate], where n=1-10, including hydrocarbon isomers, ether linkage isomers and hydroxylated derivatives thereof;
$H_2N$—NHC(=NH)—N=CH—$(CH_2)_n$-[carbohydrate], where n=1-10, including hydrocarbon isomers and hydroxylated derivatives thereof;
$H_2N$—NHC(=NH)—N=CH—$(CH_2)_n$—O—[carbohydrate], where n=1-10, including hydrocarbon isomers, ether linkage isomers and hydroxylated derivatives thereof;
$H_2N$—C(=NH)—NH—NH-[carbohydrate];
$H_2N$—C(=NH)—NH—NH—$(CH_2)_n$-[carbohydrate], where n=1-10, including hydrocarbon isomers and hydroxylated derivatives thereof;
$H_2N$—C(=NH)—NH—NH—$(CH_2)_n$—O-[carbohydrate], where n=1-10, including hydrocarbon isomers, ether linkage isomers and hydroxylated derivatives thereof;
$H_2N$—C(=NH)—NH—N=CH—$(CH_2)_n$-[carbohydrate], where n-1-10, including hydrocarbon isomers and hydroxylated derivatives thereof;

H$_2$N—C(=NH)—NH—N=CH—(CH$_2$)$_n$—O-[carbohydrate], where n=1-10, including hydrocarbon isomers, ether linkage isomers and hydroxylated derivatives thereof;

b. primary amine, aminoguanidine and guanidine derivatives of sucrose polyesters having one or more carbonyl trapping functional group per molecule wherein each carbonyl trapping functional group is in the ω-, ω-1 or other isomeric position within the fatty acyl chains, wherein each fatty acyl chain may have from 3 to 26 carbons, from one to five nitrogen functional groups and from one to 24 hydroxyl groups;

c. mixed polysaccharide polymeric derivatives wherein primary amine, aminoalkyl with one to ten carbons per alkyl group, amino-hydroxyalkyl with one to ten carbons per alkyl group and one to ten hydroxyl groups per alkyl group, aminoguanidine, aminoguanidinyl-alkyl with one to ten carbons per alkyl group, aminoalkylguanidinyl aminoalkyl with one to ten carbons per alkyl group, guanidine, aminobenzene and/or aminoalkyl with one to ten carbons per alkyl group, wherein the functional groups are covalently attached to matrices; and d. non-polysaccharide polymeric derivatives wherein primary amine, aminoalkyl with one to ten carbons per alkyl group, amino-hydroxyalkyl with one to ten carbons per alkyl group and one to ten hydroxyl groups per alkyl group, aminoguanidine, aminoguanidinyl-alkyl with one to ten carbons per alkyl group, aminoalkylguanidinyl aminoalkyl with one to ten carbons per alkyl group, guanidine, aminobenzene and/or aminoalkyl with one to ten carbons per alkyl group, wherein functional groups are covalently attached to a synthetic nondigestible polymer selected from the group consisting of polystyrene, styrene-divinylbenzene copolymer, polyvinyl alcohol and crosslinked derivatives thereof, and wherein hydrocarbon spacer groups are selected from alkene and alkyl groups.

2. A method of treating a mammalian subject suffering from a chronic inflammatory disease, comprising administering to the subject a composition according to claim 1.

3. The method of claim 2 wherein the required primary agent is used in a dosage range of from about 15 mg/kg/day to about 450 mg/kg/day.

4. The method of claim 2 wherein said chronic inflammatory disease is selected from the group consisting of: chronic gingivitis; chronic periodontitis; chronic autoimmune gastritis; ileitis, Crohn's disease, inflammatory bowel disease, colitis, interstitial cystitis, psoriasis, rheumatoid arthritis, ankylosing spondylitis osteoarthritis, tendinitis; tenosynovitis; carpel tunnel syndrome and other cumulative trauma disorders; chronic discoid or systemic lupus erythematosus; pneumoconiosis due to inhalation of asbestos particles, inhalation of stone dust or quartz or inhalation of other causative agents; chronic obstructive pulmonary disease; inflammatory myopathies; inflammatory neuropathies; myasthenia gravis; multiple sclerosis; epilepsy; inflammatory site edema; post-event ischemia and reperfusion symptomology resulting from acute central nervous system trauma, stroke and spinal cord trauma; post-event consequences of kidney ischemia and reperfusion; and post-event consequences of reperfusion subsequent to myocardial infarction.

5. The method of claim 2 wherein the mammalian subject is a human.

6. The method of claim 2 wherein the subject is a non-human mammalian subject.

7. An orally administered composition comprising:
(a) a therapeutically effective amount of a pharmaceutically acceptable salt form, the free acid form, a pharmaceutically acceptable ester derivative form, or a pharmaceutically acceptable amide derivative form of at least one required primary agent of the formula:

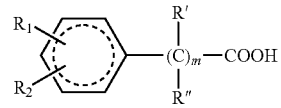

wherein R$_1$ is —NH$_2$; -aminoalkyl having 1-10 carbons; —NHC(=NH)NH$_2$; —(CH$_2$)$_n$NHC(=NH)NH$_2$ wherein n is 1-10; —C(=NH)NH$_2$; —(CH$_2$)$_n$—CH=NC(=NH)NH$_2$ wherein n is 1-10; —NHC(=NH)NHNH$_2$; —(CH$_2$)$_n$NHC(=NH)NHNH$_2$ wherein n is 1-10; —(CH$_2$)$_n$—CH=NC(=NH)NHNH$_2$ wherein n is 1-10; —NHNHC(=NH)NH$_2$; —(CH$_2$)$_n$—NHNHC(=NH)NH$_2$ wherein n is 1-10; and —(CH$_2$)$_n$—CH=N—NHC(=NH)NH$_2$ wherein n is 1-10; R$_2$ is H; —OH; —O—CH$_3$; —O—R' wherein R' is alkyl of 2-10 carbons; aminoalkyl wherein the alkyl group is 1-10 carbons; —SO$_3$H; —CH$_3$; and —(CH$_2$)$_n$CH$_3$ wherein n is 1-10; R' and R'' are —H, —OH or —CH$_3$; and m is 0 or 1; and
(b) chitin.

8. A method of treating a mammalian subject suffering from a chronic inflammatory disease, comprising administering to the subject a composition according to claim 7.

9. The method of claim 8 wherein the required primary agent is used in a dosage range of from about 15 mg/kg/day to about 450 mg/kg/day.

10. The method of claim 8 wherein said chronic inflammatory disease is selected from the group consisting of: chronic gingivitis; chronic periodontitis; chronic autoimmune gastritis; ileitis, Crohn's disease, inflammatory bowel disease, colitis, interstitial cystitis, psoriasis, rheumatoid arthritis, ankylosing spondylitis osteoarthritis, tendinitis or tenosynovitis; carpel tunnel syndrome and other cumulative trauma disorders; chronic discoid or systemic lupus erythematosus; pneumoconiosis due to inhalation of asbestos particles, inhalation of stone dust or quartz or inhalation of other causative agents; chronic obstructive pulmonary disease; inflammatory myopathies; inflammatory neuropathies; myasthenia gravis; multiple sclerosis; epilepsy; inflammatory site edema; post-event ischemia and reperfusion symptomology resulting from acute central nervous system trauma, stroke and spinal cord trauma; post-event consequences of kidney ischemia and reperfusion; and post-event consequences of reperfusion subsequent to myocardial infarction.

11. The method of claim 8 wherein the mammalian subject is a human.

12. The method of claim 8 wherein the subject is a non-human mammalian subject.

* * * * *